United States Patent
Holliday et al.

(10) Patent No.: US 9,539,143 B2
(45) Date of Patent: Jan. 10, 2017

(54) METHODS OF CORRECTING VISION

(71) Applicant: REVISION OPTICS, INC., Lake Forest, CA (US)

(72) Inventors: Keith Holliday, Lake Forest, CA (US); Alan Lang, Long Beach, CA (US)

(73) Assignee: REVISION OPTICS, INC., Lake Forest, CA (US)

( * ) Notice: Subject to any disclaimer, the term of this patent is extended or adjusted under 35 U.S.C. 154(b) by 0 days.

(21) Appl. No.: 14/656,621

(22) Filed: Mar. 12, 2015

(65) Prior Publication Data
US 2015/0250652 A1    Sep. 10, 2015

(51) Int. Cl.
*A61F 9/007* (2006.01)
*A61F 9/008* (2006.01)

(52) U.S. Cl.
CPC ....... *A61F 9/00838* (2013.01); *A61F 9/00827* (2013.01); *A61F 9/00834* (2013.01); *A61F 2009/00872* (2013.01)

(58) Field of Classification Search
CPC ...... A61F 9/013; A61F 9/007; A61F 9/00838; A61F 9/00827; A61F 9/00836; A61F 2240/001; A61F 2240/002
See application file for complete search history.

(56) References Cited

U.S. PATENT DOCUMENTS

| | | |
|---|---|---|
| 2,521,161 A | 9/1950 | Grover |
| 2,714,721 A | 8/1955 | Stone, Jr. |
| 3,091,328 A | 5/1963 | Leonardos |
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |
| 3,996,627 A | 12/1976 | Deeg et al. |
| 4,030,480 A | 6/1977 | Meyer |
| 4,037,604 A | 7/1977 | Newkirk |
| 4,039,827 A | 8/1977 | Zdrok et al. |

(Continued)

FOREIGN PATENT DOCUMENTS

| | | |
|---|---|---|
| DE | 3208729 A1 | 9/1983 |
| EP | 0308077 A2 | 3/1989 |

(Continued)

OTHER PUBLICATIONS

Sharma et al.; U.S. Appl. No. 14/211,714 entitled "Pre-treatment haze reduction for corneal inlays," filed Mar. 14, 2014.

(Continued)

*Primary Examiner* — Paul Prebilic
(74) *Attorney, Agent, or Firm* — Shay Glenn LLP

(57) ABSTRACT

Methods of correcting vision for presbyopia, including remodeling a stroma with a laser to create an intracorneal shape, where the corneal shape includes a central region with a thickness that is about 50 microns or less measured from an extension of a shape of a peripheral region of the corneal shape, wherein remodeling a portion of the stroma increases a curvature of a central portion of the anterior surface of the cornea with a central elevation change for near vision.

8 Claims, 13 Drawing Sheets

(56) References Cited

U.S. PATENT DOCUMENTS

| | | |
|---|---|---|
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,573,998 A | 3/1986 | Mazzocco |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,912 A | 6/1992 | Kaplan et al. |
| 5,123,921 A | 6/1992 | Werblin et al. |
| 5,139,518 A | 8/1992 | White |
| 5,163,934 A * | 11/1992 | Munnerlyn ......... A61F 9/00804 606/10 |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,352,233 A | 10/1994 | Anis |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,487,377 A | 1/1996 | Smith et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |
| 5,601,584 A | 2/1997 | Obagi et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,657,108 A | 8/1997 | Portney |

(56) References Cited

U.S. PATENT DOCUMENTS

| | | | |
|---|---|---|---|
| 5,682,223 A | 10/1997 | Menezes et al. |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,728,155 A | 3/1998 | Anello et al. |
| 5,732,990 A | 3/1998 | Yavitz et al. |
| 5,752,928 A | 5/1998 | de Roulhac et al. |
| 5,755,785 A | 5/1998 | Rowsey et al. |
| 5,766,181 A | 6/1998 | Chambers et al. |
| 5,772,667 A | 6/1998 | Blake |
| 5,779,711 A | 7/1998 | Kritzinger et al. |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,873,889 A | 2/1999 | Chin |
| 5,876,439 A | 3/1999 | Lee |
| 5,888,243 A | 3/1999 | Silvestrini |
| 5,913,898 A | 6/1999 | Feingold |
| 5,919,185 A | 7/1999 | Peyman |
| 5,928,245 A | 7/1999 | Wolf et al. |
| 5,929,968 A | 7/1999 | Cotie et al. |
| 5,929,969 A | 7/1999 | Roffman |
| 5,935,140 A | 8/1999 | Buratto |
| 5,941,583 A | 8/1999 | Raimondi |
| 5,944,752 A | 8/1999 | Silvestrini |
| 5,945,498 A | 8/1999 | Hopken et al. |
| 5,964,748 A * | 10/1999 | Peyman ............... A61F 2/14 606/15 |
| 5,964,776 A | 10/1999 | Peyman |
| 5,968,065 A | 10/1999 | Chin |
| 5,976,150 A | 11/1999 | Copeland |
| 5,976,168 A | 11/1999 | Chin |
| 5,980,549 A | 11/1999 | Chin |
| 6,007,510 A | 12/1999 | Nigam |
| 6,010,510 A | 1/2000 | Brown et al. |
| 6,024,448 A | 2/2000 | Wu et al. |
| 6,033,395 A | 3/2000 | Peyman |
| 6,036,714 A | 3/2000 | Chin |
| 6,050,999 A | 4/2000 | Paraschac et al. |
| 6,055,990 A | 5/2000 | Thompson |
| 6,066,170 A | 5/2000 | Lee |
| 6,068,642 A | 5/2000 | Johnson et al. |
| 6,079,826 A | 6/2000 | Appleton et al. |
| 6,083,231 A | 7/2000 | Van Noy et al. |
| 6,086,202 A | 7/2000 | Chateau et al. |
| 6,090,141 A | 7/2000 | Lindstrom |
| 6,102,946 A | 8/2000 | Nigam |
| 6,110,166 A | 8/2000 | Juhasz |
| 6,120,148 A | 9/2000 | Fiala et al. |
| 6,125,294 A | 9/2000 | Scholl et al. |
| 6,129,733 A | 10/2000 | Brady et al. |
| 6,139,560 A | 10/2000 | Kremer |
| 6,142,969 A | 11/2000 | Nigam |
| 6,143,001 A | 11/2000 | Brown et al. |
| 6,159,241 A | 12/2000 | Lee et al. |
| 6,171,324 B1 | 1/2001 | Cote et al. |
| 6,175,754 B1 | 1/2001 | Scholl et al. |
| RE37,071 E | 2/2001 | Gabrielian et al. |
| 6,183,513 B1 | 2/2001 | Guenthner et al. |
| 6,197,019 B1 | 3/2001 | Peyman |
| 6,197,057 B1 | 3/2001 | Peyman et al. |
| 6,197,058 B1 | 3/2001 | Portney |
| 6,203,538 B1 | 3/2001 | Peyman |
| 6,203,549 B1 | 3/2001 | Waldock |
| 6,203,557 B1 | 3/2001 | Chin |
| 6,206,919 B1 | 3/2001 | Lee |
| 6,210,005 B1 | 4/2001 | Portney |
| 6,214,015 B1 | 4/2001 | Reich et al. |
| 6,214,044 B1 | 4/2001 | Silverstrini |
| 6,217,571 B1 | 4/2001 | Peyman |
| 6,221,067 B1 | 4/2001 | Peyman |
| 6,228,113 B1 | 5/2001 | Kaufman |
| 6,228,114 B1 | 5/2001 | Lee |
| 6,248,111 B1 | 6/2001 | Glick et al. |
| 6,250,757 B1 | 6/2001 | Roffman et al. |
| 6,251,114 B1 | 6/2001 | Farmer et al. |
| 6,264,648 B1 | 7/2001 | Peyman |
| 6,264,670 B1 | 7/2001 | Chin |
| 6,264,692 B1 | 7/2001 | Woffinden et al. |
| 6,267,768 B1 | 7/2001 | Deacon et al. |
| 6,271,281 B1 | 8/2001 | Liao et al. |
| 6,277,137 B1 | 8/2001 | Chin |
| 6,280,449 B1 | 8/2001 | Blake |
| 6,280,470 B1 | 8/2001 | Peyman |
| 6,283,595 B1 | 9/2001 | Breger |
| 6,302,877 B1 | 10/2001 | Ruiz |
| 6,325,509 B1 | 12/2001 | Hodur et al. |
| 6,325,792 B1 | 12/2001 | Swinger et al. |
| 6,350,272 B1 | 2/2002 | Kawesch |
| 6,361,560 B1 | 3/2002 | Nigam |
| 6,364,483 B1 | 4/2002 | Grossinger et al. |
| 6,371,960 B2 | 4/2002 | Heyman et al. |
| 6,391,230 B1 | 5/2002 | Sarbadhikari |
| 6,398,277 B1 | 6/2002 | McDonald |
| 6,398,789 B1 | 6/2002 | Capetan |
| 6,428,572 B2 | 8/2002 | Nagai |
| 6,435,681 B2 | 8/2002 | Portney |
| 6,436,092 B1 | 8/2002 | Peyman |
| 6,447,519 B1 | 9/2002 | Brady et al. |
| 6,447,520 B1 | 9/2002 | Ott et al. |
| 6,458,141 B1 | 10/2002 | Peyman |
| 6,461,384 B1 | 10/2002 | Hoffmann et al. |
| 6,471,708 B2 | 10/2002 | Green |
| 6,474,814 B1 | 11/2002 | Griffin |
| 6,506,200 B1 | 1/2003 | Chin |
| 6,511,178 B1 | 1/2003 | Roffman et al. |
| 6,527,389 B2 | 3/2003 | Portney |
| 6,537,283 B2 | 3/2003 | Van Noy |
| 6,543,610 B1 | 4/2003 | Nigam |
| 6,544,286 B1 | 4/2003 | Perez |
| 6,551,307 B2 | 4/2003 | Peyman |
| 6,554,424 B1 | 4/2003 | Miller et al. |
| 6,554,425 B1 | 4/2003 | Roffman et al. |
| 6,557,998 B2 | 5/2003 | Portney |
| 6,581,993 B2 | 6/2003 | Nigam |
| 6,582,076 B1 | 6/2003 | Roffman et al. |
| 6,589,057 B1 | 7/2003 | Keenan et al. |
| 6,589,203 B1 | 7/2003 | Mitrev |
| 6,589,280 B1 * | 7/2003 | Koziol ............... A61F 9/013 606/5 |
| 6,592,591 B2 | 7/2003 | Polla et al. |
| 6,596,000 B2 | 7/2003 | Chan et al. |
| 6,605,093 B1 | 8/2003 | Blake |
| 6,607,537 B1 | 8/2003 | Binder |
| 6,607,556 B1 | 8/2003 | Nigam |
| 6,623,522 B2 | 9/2003 | Nigam |
| 6,626,941 B2 | 9/2003 | Nigam |
| 6,629,979 B1 | 10/2003 | Feingold et al. |
| 6,632,244 B1 | 10/2003 | Nigam |
| 6,641,577 B2 | 11/2003 | Bille |
| 6,645,246 B1 | 11/2003 | Weinschenk, III et al. |
| 6,648,877 B1 | 11/2003 | Juhasz et al. |
| 6,657,029 B2 | 12/2003 | Vanderbilt |
| 6,666,887 B1 | 12/2003 | Callahan et al. |
| 6,673,112 B2 | 1/2004 | Nigam |
| 6,702,807 B2 | 3/2004 | Peyman |
| 6,709,103 B1 | 3/2004 | Roffman et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,733,526 B2 | 5/2004 | Paul et al. |
| 6,808,262 B2 | 10/2004 | Chapoy et al. |
| 6,824,178 B2 | 11/2004 | Nigam |
| 6,849,090 B2 | 2/2005 | Nigam |

(56) References Cited

U.S. PATENT DOCUMENTS

| | | |
|---|---|---|
| 6,855,163 B2 | 2/2005 | Peyman |
| 6,875,232 B2 | 4/2005 | Nigam |
| 6,879,402 B2 | 4/2005 | Küchel |
| 6,881,197 B1 | 4/2005 | Nigam |
| 6,893,461 B2 | 5/2005 | Nigam |
| 6,949,093 B1 | 9/2005 | Peyman |
| 6,955,432 B2 | 10/2005 | Graham |
| 7,128,351 B2 | 10/2006 | Nigam |
| 7,585,075 B2 | 9/2009 | Marmo |
| 7,699,837 B2 | 4/2010 | Cox et al. |
| 7,776,086 B2 | 8/2010 | Miller |
| 7,976,577 B2 | 7/2011 | Silvestrini |
| 7,992,906 B2 | 8/2011 | Nigam |
| 8,057,541 B2 | 11/2011 | Dishler et al. |
| 8,162,953 B2 | 4/2012 | Dishler et al. |
| 8,469,948 B2 | 6/2013 | Dishler et al. |
| 8,540,727 B2 | 9/2013 | Dishler et al. |
| 8,668,735 B2 | 3/2014 | Nigam et al. |
| 8,685,292 B2 | 4/2014 | Mandler et al. |
| 8,900,296 B2 | 12/2014 | Holliday et al. |
| 9,005,280 B2 | 4/2015 | Nigam |
| 2001/0027314 A1 | 10/2001 | Peyman |
| 2001/0051826 A1 | 12/2001 | Bogaert et al. |
| 2002/0010510 A1 | 1/2002 | Silvestrini |
| 2002/0055753 A1 | 5/2002 | Silvestrini |
| 2002/0101563 A1 | 8/2002 | Miyamura et al. |
| 2002/0103538 A1 | 8/2002 | Hughes et al. |
| 2002/0135733 A1* | 9/2002 | Portney ............... A61F 2/1618 351/159.41 |
| 2002/0138069 A1 | 9/2002 | Peyman |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0176855 A1* | 9/2003 | Gross .................. A61F 9/008 606/5 |
| 2003/0208190 A1 | 11/2003 | Roberts et al. |
| 2003/0220653 A1 | 11/2003 | Perez |
| 2003/0229303 A1 | 12/2003 | Haffner et al. |
| 2004/0010278 A1 | 1/2004 | Nakamura et al. |
| 2004/0019379 A1 | 1/2004 | Glick et al. |
| 2004/0034413 A1 | 2/2004 | Christensen |
| 2004/0054408 A1 | 3/2004 | Glick et al. |
| 2004/0073303 A1 | 4/2004 | Schanzlin et al. |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0182488 A1 | 8/2005 | Peyman |
| 2005/0203494 A1 | 9/2005 | Holliday |
| 2005/0222679 A1 | 10/2005 | Peyman |
| 2005/0246015 A1* | 11/2005 | Miller .................. A61F 2/14 623/5.11 |
| 2005/0246016 A1 | 11/2005 | Miller et al. |
| 2006/0004381 A1 | 1/2006 | Feingold et al. |
| 2006/0020267 A1 | 1/2006 | Marmo |
| 2006/0116762 A1 | 6/2006 | Hong et al. |
| 2006/0134170 A1 | 6/2006 | Griffith et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0038276 A1 | 2/2007 | Yaldo |
| 2007/0106318 A1 | 5/2007 | McDonald |
| 2007/0106376 A1 | 5/2007 | Roberts et al. |
| 2007/0129797 A1 | 6/2007 | Lang et al. |
| 2007/0182920 A1 | 8/2007 | Back et al. |
| 2007/0244559 A1 | 10/2007 | Shiuey |
| 2007/0255401 A1 | 11/2007 | Lang |
| 2007/0280994 A1 | 12/2007 | Cunanan |
| 2008/0039825 A1* | 2/2008 | Lai ..................... A61B 3/107 606/5 |
| 2008/0262610 A1 | 10/2008 | Lang et al. |
| 2008/0269771 A1 | 10/2008 | Fulcher |
| 2008/0275433 A1* | 11/2008 | Russmann ............ A61F 9/008 606/5 |
| 2008/0281304 A1 | 11/2008 | Campbell |
| 2009/0005764 A1 | 1/2009 | Knox et al. |
| 2009/0079940 A1 | 3/2009 | Dai et al. |
| 2009/0216217 A1 | 8/2009 | Odrich et al. |
| 2009/0326650 A1 | 12/2009 | Zickler et al. |
| 2010/0210996 A1* | 8/2010 | Peyman ................ A61F 7/007 604/20 |
| 2010/0241060 A1 | 9/2010 | Roizman et al. |
| 2010/0331831 A1 | 12/2010 | Bischoff et al. |
| 2011/0029073 A1* | 2/2011 | Liang .................. A61F 2/147 623/5.11 |
| 2011/0149241 A1 | 6/2011 | Dai |
| 2011/0208300 A1 | 8/2011 | de Juan et al. |
| 2011/0218623 A1 | 9/2011 | Dishler et al. |
| 2011/0256806 A1 | 10/2011 | Monnoyeur |
| 2011/0290681 A1 | 12/2011 | Nigam |
| 2011/0319876 A1* | 12/2011 | Feingold ............ A61F 9/00836 606/4 |
| 2012/0231416 A1 | 9/2012 | Drapeau et al. |
| 2012/0238806 A1 | 9/2012 | Mangiardi et al. |
| 2012/0245592 A1 | 9/2012 | Berner et al. |
| 2013/0023892 A1 | 1/2013 | Schneider et al. |
| 2013/0060255 A1 | 3/2013 | Feingold et al. |
| 2013/0211523 A1 | 8/2013 | Southard et al. |
| 2013/0231739 A1 | 9/2013 | Dishler et al. |
| 2013/0253527 A1 | 9/2013 | Schneider et al. |
| 2013/0253529 A1 | 9/2013 | Walter et al. |
| 2013/0281993 A1 | 10/2013 | Dishler et al. |
| 2013/0317605 A1 | 11/2013 | Ide et al. |
| 2013/0324983 A1 | 12/2013 | Liang |
| 2013/0331935 A1* | 12/2013 | Krause ................. A61F 2/142 623/5.11 |
| 2014/0128855 A1 | 5/2014 | Wottke et al. |
| 2014/0135915 A1 | 5/2014 | Nigam et al. |
| 2014/0200665 A1 | 7/2014 | Lang et al. |
| 2014/0257477 A1 | 9/2014 | Plambeck et al. |
| 2014/0288540 A1 | 9/2014 | Bischoff et al. |
| 2015/0080865 A1 | 3/2015 | Holliday et al. |

FOREIGN PATENT DOCUMENTS

| | | |
|---|---|---|
| EP | 0420549 A2 | 4/1991 |
| EP | 0729323 B1 | 7/1998 |
| EP | 0668061 B1 | 9/2000 |
| JP | S5973622 A | 4/1984 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2002537895 | 11/2002 |
| JP | 03-508135 | 3/2003 |
| JP | 2007500070 | 1/2007 |
| WO | WO92/08423 A1 | 5/1992 |
| WO | WO93/05731 A1 | 4/1993 |
| WO | WO96/26690 A1 | 9/1996 |
| WO | WO98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO 2005/107648 A2 | 11/2005 |
| WO | WO 2006/029316 A1 | 4/2006 |

(56) References Cited

FOREIGN PATENT DOCUMENTS

| WO | WO 2006/060363 A2 | 6/2006 |
|----|-------------------|--------|
| WO | WO 2007/101016 A2 | 9/2007 |
| WO | WO 2007/132332 A2 | 11/2007 |

OTHER PUBLICATIONS

Esguerra et al.; U.S. Appl. No. 14/463,355 entitled "Corneal implant storage, packaging, and delivery devices," filed Aug. 19, 2014.
Collins et al.; U.S. Appl. No. 14/575,833 entitled "Integrated part fixturing for lathing processes," filed Dec. 18, 2014.
Sharma; U.S. Appl. No. 14/427,510 entitled "Corneal implant edges and methods of use," filed Mar. 11, 2015.
Alio, J. J., et al., "Intracorneal Inlay Complicated by Intrastomal Epithelial Opacification," Arch Ophthalmol, Oct. 2004; vol. 122; 6 pages.
Cheng, et al.; "Predicting subjective judgment of best focus with objective image quality metrics"; Journal of Vision; Apr. 23, 2004; vol. 4(4); pp. 310-321.
Churms, P.W., "The Theory and Computation of Optical Modifications to the Cornea in Refractive Keratoplasty," American Journal of Optometry & Physiological Optics, 56:2, pp. 67-74, Feb. 1979.
Dymax; UV curable optical assembly; 2 pages; retrieved Mar. 4, 2015 from the internet (http:www.dymax.com/index.php/adhesives/optical).
Huang et al.; Mathematical Model of Corneal Surface Smoothing After Laser Refractive Surgery; American Journal of Ophthalmology; Mar. 2003; pp. 267-278.
Lang, A.J. et al., "First order design of intracorneal inlays: dependence on keratometric flap and corneal properties," ARVO Abstracts 2006, poster No. 3591, May 3, 2006.
Liou, H. L. et al., "Anatomically accurate, finite model eye for optical modeling", Journal of the Optical Society of America, vol. 14, No. 8, Aug. 1997.
Jankov et al.; Laser intrastromal keratoplasty—case report; J. Refract.Surg.; 20(1); pp. 79-84; Jan.-Feb. 2004.
Marsack,et al.; "Metrics of optical quality derived from wave aberrations predict visual performance"; Journal of Vision; Apr. 23, 2004; vol. 4(4); pp. 322-328.
Navarro et al.; Accommodation-dependent model of the human eye with aspherics; J. Opt. Soc Am. A; vol. 2; No. 8; Aug. 1985; pp. 1273-1281.
Petroll et al.; Confocal assessment of the cornal response to intracorneal lens insertion and laser in situ keratomileusis with flap creation using IntraLase; J Cataract Refract Surg; vol. 32; pp. 1119-1128; Jul. 2006.
Reinstein et al.; Change in epithelial thickness profile 24 hours and longitudinally for 1 year after myopic LASIK: three-dimensional display with Artemis very high-frequency digital ultrasound; J Refract Surg. Mar. 2012; 28(3):195-201.
Reinstein et al.; Epithelial thickness up to 26 years after radial keratotomy: three-dimensional display with Artemis very high-frequency digital ultrasound; J Refract Surg. Aug. 2011; 27(8):618-624.
Reinstein et al.; Epithelial, stromal, and total corneal thickness in keratoconus: three-dimensional display with artemis very-high frequency digital ultrasound; J Refract Surg. Apr. 2010; 26(4):259-71.
Reinstein et al.; Epithelial thickness after hyperopic LASIK: three-dimensional display with Artemis very high-frequency digital ultrasound; J Refract Surg. Aug. 2010;26(8):555-64.
Reinstein et al.; Corneal epithelial thickness profile in the diagnosis of keratoconus; J Refract Surg. Jul. 2009; 25(7):604-10.
Reinstein et al.; Stability of LASIK in topographically suspect keratoconus confirmed non-keratoconic by Artemis VHF digital ultrasound epithelial thickness mapping: 1-year follow-up; J Refract Surg. Jul. 2009; 25(7):569-77.
Reinstein et al.; Epithelial, stromal, and corneal pachymetry changes during orthokeratology; Optom Vis Sci. Aug. 2009; 86(8):E1006-14.
Reinstein et al.; Epithelial thickness profile changes induced by myopic LASIK as measured by Artemis very high-frequency digital ultrasound; J Refract Surg. May 2009; 25(5):444-50 (Author manusript).
Reinstein et al.; Epithelial thickness in the normal cornea: three-dimensional display with Artemis very high-frequency digital ultrasound; J Refract Surg. Jun. 2008; 24(6):571-81 (Author manusript).
Reinstein et al.; Epithelial and stromal changes induced by intacs examined by three-dimensional very high-frequency digital ultrasound; J Refract Surg. May-Jun. 2001; 17(3):310-8.
Reinstein et al.; Epithelial and corneal thickness measurements by high-frequency ultrasound digital signal processing; Ophthalmology. Jan. 1994; 101(1):140-6.
Reinstein et al.; High-frequency ultrasound measurement of the thickness of the corneal epithelium; Refract Corneal Surg. Sep.-Oct. 1993;9(5):385-7.
Serrao et al.; Corneal epithelial healing after photorefractive keratectomy: analytical study; J. Cataract Refract Surg; vol. 31(5); pp. 930-937; May 2005.
Thoft et al.; The X, Y, Z Hypothesis of Corneal Epithelial Maintenance; Investigative Ophthalmology & Visual Science; vol. 24; pp. 1442-1443; Oct. 1983.
Watsky, M.A. et al., "Predicting Refractive Alterations with Hydrogel Keratophakia," Investigative Opthalmology & Visual Science, vol. 26, pp. 240-243, Feb. 1985.
Winn et al.; Factors affecting light-adapted pupil size in normal human subjects; Investigative Ophthalmology and Visual Science; 35(3); pp. 1132-1137; Mar. 1994.
Gouveria et al.; Fabrication of a bio-prosthetic cornea from human keratocytes; IOVS; 55(13); 6 pages; retrieved from the internet (http:/iovs.arovojournals.org/article.aspx?articleid=2270729>); Apr. 2014.
Esguerra et al.; U.S. Appl. No. 14/688,226 entitled "Corneal implant delivery devices and methods of use," filed Apr. 16, 2015.

* cited by examiner

| Subject | Postop ucnVA | PostucNL | PostOp ucDVA | PostucDL | InlayADDeff | InlayCen2.5mmSph | Diff Fit Ht | Diff Eff Dia |
|---|---|---|---|---|---|---|---|---|
| 1 | 32 | 3 | 20 | 1 | 0.75 | -2.32 | 5.9 | 3.7 |
| 2 | 40 | 3 | 40 | -2 | 1.00 | -2.72 | 6.7 | 3.7 |
| 3 | 28 | 4 | 51 | -3 | 1.75 | -2.47 | 8.2 | 4.4 |
| 4 | 25 | 3 | 64 | -5 | 1.75 | -2.99 | 9.3 | 4.3 |
| 5 | 27 | 3 | 25 | -1 | 2.50 | -2.19 | 6.2 | 3.9 |
| 6 | 21 | 5 | 25 | -1 | 2.25 | -2.78 | 6.7 | 3.8 |
| 7 | 22 | 4 | 32 | -2 | 1.25 | -2.38 | 5.3 | 3.0 |
| 8 | 28 | 5 | 32 | -2 | 1.50 | -1.99 | 4.7 | 3.8 |
| 9 | 24 | 5 | 40 | -2 | 2.00 | -2.37 | 6.2 | 3.9 |
| Average = | 27 | 4 | 37 | -2 | 1.64 | -2.47 | 6.6 | 3.9 |
| Max = | 40 | 5 | 64 | 1 | 2.50 | -1.99 | 9.3 | 4.4 |
| Min = | 21 | 3 | 20 | -5 | 0.75 | -2.99 | 4.7 | 3.0 |
| Stdev = | 6 | 1 | 14 | 2 | 0.57 | 0.31 | 1.4 | 0.4 |

FIG. 7

| Subject | Postop ucnVA | PostucNL | PostOP ucDVA | PostucDL | InlayADDeff | InlayCen2.5mmSph | Diff Fit Ht | Diff Eff Dia |
|---|---|---|---|---|---|---|---|---|
| 1 | 20 | 4.4 | 40 | -2.8 | 2.75 | -2.68 | 6.7 | 3.6 |
| 2 | 25 | 4.6 | 35 | -2.0 | 2.88 | -1.87 | 6.3 | 4.2 |
| 3 | 25 | 5.4 | 33 | -1.8 | 1.38 | -1.82 | 5.5 | 4.0 |
| 4 | 20 | 6.0 | 42 | -3.0 | 2.13 | -2.34 | 6.9 | 4.0 |
| 5 | 25 | 5.8 | 29 | -1.0 | 2.00 | -1.82 | 6.0 | 4.4 |
| 6 | 21 | 4.8 | 80 | -4.0 | 2.25 | -1.60 | 5.8 | 3.8 |
| 7 | 20 | 5.0 | 32 | -1.6 | 2.75 | -2.38 | 6.3 | 4.2 |
|  |  |  |  |  |  |  |  |  |
| Average = | 22 | 5.1 | 42 | -2.3 | 2.30 | -2.08 | 6.2 | 4.0 |
| Max = | 25 | 6.0 | 80 | -1.0 | 2.88 | -1.60 | 6.9 | 4.4 |
| Min = | 20 | 4.4 | 29 | -4.0 | 1.38 | -2.68 | 5.5 | 3.6 |
| Stdev = | 3 | 0.6 | 18 | 1.0 | 0.53 | 0.39 | 0.5 | 0.3 |

FIG. 9

METHODS OF CORRECTING VISION

CROSS REFERENCE TO RELATED APPLICATIONS

The following applications and publications are incorporated by reference herein: U.S. Pat. No. 8,057,541, issued Nov. 15, 2011; U.S. Pub. No. 2011/0218623, published Sep. 8, 2011; and U.S. Pub. No. 2008/0262610, published Oct. 23, 2008.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Abnormalities in the human eye can lead to vision impairment such as myopia (near-sightedness), hyperopia (far-sightedness), astigmatism, and presbyopia. A variety of devices and procedures have been developed to attempt to address these abnormalities.

One type of device that has been proposed is a corneal implant, such as an onlay, which is placed on top of the cornea such that the outer layer of the cornea (i.e., the epithelium), can grow over and encompass the onlay. An inlay is a corneal implant that is surgically implanted within the cornea beneath a portion of corneal tissue by, for example, cutting a flap in the cornea and positioning the inlay beneath the flap. An inlay can also be positioned within a pocket formed in the cornea.

Inlays can alter the refractive power of the cornea by changing the shape of the anterior surface of the cornea, by creating an optical interface between the cornea and an implant by having an index of refraction different than that of the cornea (i.e., has intrinsic power), or both. The cornea is the strongest refracting optical element in the eye, and altering the shape of the anterior surface of the cornea can therefore be a particularly useful method for correcting vision impairments caused by refractive errors.

LASIK (laser-assisted in situ keratomileusis) is a type of refractive laser eye surgery in which a laser is used to remodel a portion of the cornea after lifting a previous cut corneal flap.

Presbyopia is generally characterized by a decrease in the eye's ability to increase its power to focus on nearby objects due to, for example, a loss of elasticity in the crystalline lens that occurs over time. Ophthalmic devices and/or procedures (e.g., contact lenses, intraocular lenses, LASIK, inlays) can be used to address presbyopia using three common approaches. With a monovision prescription, the diopter power of one eye is adjusted to focus distant objects and the power of the second eye is adjusted to focus near objects. The appropriate eye is used to clearly view the object of interest. In the next two approaches, multifocal or bifocal optics are used to simultaneously, in one eye, provide powers to focus both distant and near objects. One common multifocal design includes a central zone of higher diopter power to focus near objects, surrounded by a peripheral zone of the desired lower power to focus distant objects. In a modified monovision prescription, the diopter power of one eye is adjusted to focus distance objects, and in the second eye a multifocal optical design is induced by the intracorneal inlay. The subject therefore has the necessary diopter power from both eyes to view distant objects, while the near power zone of the multifocal eye provides the necessary power for viewing near objects. In a bilateral multifocal prescription, the multifocal optical design is induced in both eyes. Both eyes therefore contribute to both distance and near vision.

Regardless of the vision correction procedure and/or devices implanted, it is important to understand the cornea's natural response to the procedure to understand how the cornea will attempt to reduce or minimize the impact of the vision correction procedure.

Specific to understanding a response to an inlay, Watsky et al. proposed a simple biomechanical response in Investigative Ophthalmology and Visual Science, vol. 26, pp. 240-243 (1985). In this biomechanical model ("Watsky model"), the anterior corneal surface radius of curvature is assumed to be equal to the thickness of the lamellar corneal material (i.e., flap) between the anterior corneal surface and the anterior surface of a corneal inlay plus the radius of curvature of the anterior surface of the inlay.

Reviews of clinical outcomes for implanted inlays or methods for design generally discuss relatively thick inlays (e.g., greater than 200 microns thick) for which the above simple biomechanical response model has some validity. This is because the physical size of the inlay dominates the biomechanical response of the cornea and dictates the primary anterior surface change. When an inlay is relatively small and thin, however, the material properties of the cornea contribute significantly to the resulting change in the anterior corneal surface. Petroll et al. reported that implantation of inlays induced a thinning of the central corneal epithelium overlying the inlay. "Confocal assessment of the corneal response to intracorneal lens insertion and laser in situ keratomileusis with flap creation using IntraLase," J. Cataract Refract. Surg., vol. 32, pp 1119-1128 (July 2006).

Huang et al. reported central epithelial thickening after myopic ablation procedures and peripheral epithelial thickening and central epithelial thinning after hyperopic ablation procedures. "Mathematical Model of Corneal Surface Smoothing After Laser Refractive Surgery," America Journal of Ophthalmology, March 2003, pp 267-278. The theory in Huang does not address correcting for presbyopia, nor does it accurately predict changes to the anterior surface which create a center near portion of the cornea for near vision while allowing distance vision in an area of the cornea peripheral to the center near portion. Additionally, Huang reports on removing cornea tissue by ablation as opposed to adding material to the cornea, such as an intracorneal inlay.

What is needed is an understanding of the cornea's response to the correction of presbyopia. An understanding of the corneal response allows the response to be compensated for when performing the procedure on the cornea and/or implanting an implant within the cornea, either of which can be used to alter the curvature of the cornea. A need also exists for understanding the cornea's response to a vision correction procedure that creates a center zone for near vision while providing distance vision in a region peripheral to the central zone.

SUMMARY OF THE DISCLOSURE

One aspect of the disclosure is a method of correcting vision for presbyopia, comprising: remodeling the stroma with a laser to create an intracorneal shape, wherein the corneal shape includes a central region with a thickness that is about 50 microns or less measured from an extension of a shape of a peripheral region of the corneal shape, wherein remodeling a portion of the stroma increases a curvature of a central portion of the anterior surface of the cornea with a central elevation change for near vision while allowing distance vision in a region peripheral to the central portion; wherein the corneal shape compensates for epithelial remodeling of the epithelial layer of the cornea in response to remodeling the stroma, and wherein the central region with a thickness that is about 50 microns or less measured from an extension of a shape of the peripheral region of the corneal ablation shape is 3 to 7 times the central elevation change.

In some embodiments the remodeling step is performed without ablating the stroma.

In some embodiments the remodeling step creates a corneal lenticule, and the intracorneal shape is defined by a posterior lenticule incision.

One aspect of the disclosure is a method of correcting vision for presbyopia, comprising: creating a lenticule in a stroma, wherein creating the lenticule includes creating an anterior lenticule incision and a posterior lenticule incision with a femtosecond laser, wherein one of the posterior lenticule incision and the anterior lenticule incision has a central region and a peripheral region, the central region having increased curvature relative to the peripheral region, and a central thickness that is about 50 microns or less measured from an extension of the peripheral region, the central region having an outer diameter between 1 mm and 4 mm; and removing the lenticule from the stroma, wherein removing the lenticule increases the curvature of a central portion of the anterior surface of the cornea with a central elevation change for near vision; wherein one of the posterior lenticule incision and anterior lenticule incision compensates for epithelial remodeling of the epithelial layer of the cornea in response to cutting and removing the lenticule in the stroma, and wherein the central thickness that is about 50 microns or less measured from an extension of the peripheral region is 3 to 7 times the central elevation change.

In some embodiments creating the anterior lenticule incision comprises creating the anterior lenticule incision between 5 microns and 250 microns deep in the stroma.

In some embodiments removing the lenticule comprises creating a corneal flap.

In some embodiments the method of correcting vision does not include creating a corneal flap.

One aspect of the disclosure is a method of correcting vision for presbyopia, comprising: creating a lenticule in a stroma, wherein creating the lenticule includes creating an anterior lenticule incision and a posterior lenticule incision with a femtosecond laser, wherein the posterior lenticule incision has a posterior peripheral region and a posterior central region, and the anterior lenticule incision has an anterior central region and an anterior peripheral region, the anterior and posterior central regions having increased curvature relative to the anterior and posterior peripheral regions, the anterior and posterior central regions having a combined thickness that is about 50 microns or less measured from extension of the peripheral regions, the anterior and posterior central regions having an outer diameter between 1 mm and 4 mm; and removing the lenticule from the stroma, wherein removing the lenticule increases the curvature of a central portion of the anterior surface of the cornea with a central elevation change for near vision; wherein the posterior lenticule incision and the anterior lenticule incision compensate for epithelial remodeling of the epithelial layer of the cornea in response to cutting and removing the lenticule in the stroma, and wherein the combined central thickness that is about 50 microns or less measured from extensions of the peripheral regions is 3 to 7 times the central elevation change.

BRIEF DESCRIPTION OF THE DRAWINGS

FIGS. 7 and 9 present clinical data (e.g., distance and near visual acuity and the refractive effect created by the inlay) and the change in anterior corneal surface elevation derived from pre-op and post-op wavefront measurements of patients in which an inlay was implanted.

DETAILED DESCRIPTION

This disclosure relates to methods of vision correction and methods of compensating for a cornea's response to the vision correction procedure to invoke a desired corneal shape change. The disclosure includes methods of correcting presbyopia. In some embodiments the methods include implanting a corneal inlay within cornea tissue to correct for presbyopia while compensating for the inlay's presence within the cornea. The disclosure also provides methods of increasing the curvature of a central portion of the anterior surface of the cornea to provide near vision in the central portion while providing distance vision peripheral to the central portion. In some particular embodiments an inlay is implanted in the cornea to cause the central portion to increase in curvature to provide near vision.

The cornea can be generally considered to be comprised of, from the anterior A to posterior P direction, the epithelium, Bowman's layer, stroma, Descemet's membrane, and the endothelium. The epithelium is a layer of cells that can be thought of as covering the surface of the cornea and it is only about five (5) cells thick with a thickness of about 50 microns. The stroma is the thickest layer of the cornea and gives the cornea much of its strength, and most refractive surgeries involve manipulating stroma cells. Descemet's membrane and the endothelium are considered the posterior portion of the cornea and are generally not discussed herein. The instant disclosure focuses the discussion on the epithelium, Bowman's layer, and the stroma.

As disclosed herein a cornea's response to a vision correction procedure is generally described as a "physiological response," or variations thereof. The physiological response may include any biomechanical response, which is the corneal response due to an interaction with and/or alteration to Bowman's layer. A physiological response as used herein may also include an epithelial response, which includes a natural remodeling of the epithelial layer in response to a vision correction procedure.

Figure 1:
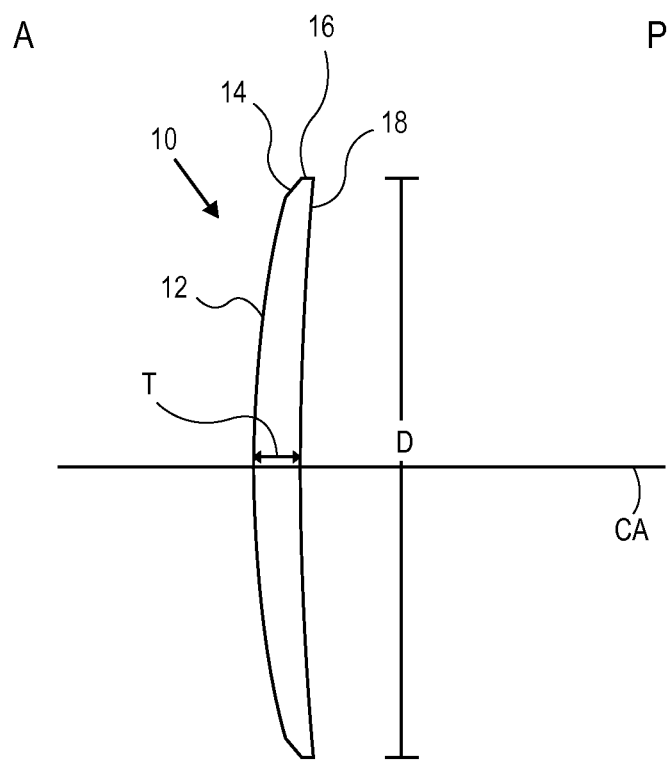
FIG. 1 shows an exemplary intracorneal inlay which can be implanted within cornea tissue according to methods herein.

In some embodiments a corneal inlay is used to correct for presbyopia. FIG. 1 is a side cross-sectional view of an exemplary corneal inlay 10 with diameter D, central thickness T along the central axis CA of the inlay, anterior surface 12, posterior surface 18, outer edge 16, and optional beveled portion 14. Anterior surface 12 has an anterior radius of curvature, and posterior surface 18 has a posterior radius of curvature. Outer edge 16 connects posterior surface 18 and beveled portion 14. The beveled portion may be considered a part of the anterior surface or may be considered a separate surface between the anterior surface and the posterior surface. Exemplary inlay 10 can be used to treat, for example without limitation, presbyopia.

Inlay 10 can have any features or parameters described herein or in any of the following Patent Applications and Patents: U.S. patent application Ser. No. 11/738,349, filed Apr. 20, 2007, (U.S. Patent Application No. US 2008/0262610 A1), U.S. patent application Ser. No. 11/381,056, filed May 1, 2006 (Patent Application Pub. US 2007/0255401 A1), U.S. patent application Ser. No. 11/554,544, filed Oct. 30, 2006 (Patent Application Pub. US 2007/0203577 A1), U.S. patent application Ser. No. 11/293,644, filed Dec. 1, 2005 (Patent Application Pub. US 2007/0129797 A1), U.S. patent application Ser. No. 11/421,597, filed Jun. 1, 2006 (Patent Application Pub. US 2007/0280994 A1), Ser. No. 10/924,152, filed Aug. 23, 2004 (Patent Application Pub. US 2005/0178394 A1), U.S. patent application Ser. No. 11/106,983, filed Apr. 15, 2005 (Patent Application Pub. US 2005/0246016 A1), U.S. patent application Ser. No. 10/837,402, filed Apr. 30, 2004 (Patent Application Pub. US 2005/0246015 A1), U.S. patent application Ser. No. 10/053,178, filed Nov. 7, 2001 (U.S. Pat. No. 6,623,522), U.S. patent application Ser. No. 10/043,975, filed Oct. 19, 2001 (U.S. Pat. No. 6,626,941), U.S. patent application Ser. No. 09/385,103, filed Aug. 27, 1999 (U.S. Pat. No. 6,361,560), and U.S. patent application Ser. No. 09/219,594, filed Dec. 23, 1998 (U.S. Pat. No. 6,102,946), all of which are incorporated by reference herein.

Inlay 10 can be implanted within the cornea by known procedures such as by cutting a flap 25 (see FIG. 2) in the cornea, lifting the flap 25 to expose the corneal bed, placing the inlay 10 on the exposed cornea bed, and repositioning the flap 25 over the inlay 10. When flap 25 is cut, a small section of corneal tissue is left intact, creating a hinge for flap 25 so that flap 25 can be repositioned accurately over the inlay 20. After the flap 25 is repositioned over the inlay, the flap adheres to the corneal bed. In some embodiments in which an inlay is positioned beneath a flap, the inlay is implanted between about 100 microns and about 200 microns deep in the cornea. In some embodiments the inlay is positioned at a depth of between about 130 microns to about 160 microns. In some particular embodiments the inlay is implanted at a depth about 150 microns.

The inlay can also be implanted by creating a pocket in the cornea and positioning the inlay within the formed pocket. Pockets are generally created deeper in the cornea than flaps, which can help in preventing nerve damage. In some embodiments in which a pocket is formed, the inlay is implanted at a depth of between about 150 microns and about 300 microns. In some embodiments the inlay is positioned at a depth of between about 200 microns to about 250 microns.

The inlay should be positioned on the corneal bed with the inlay centered on the subject's pupil or visual axis. Inlay 10 can be implanted in the cornea at a depth of about 50% or less of the cornea thickness measured from the anterior surface of the cornea (approximately 250 µm or less). The flap 25 may be cut using, for example, a laser (e.g., a femtosecond laser) or a mechanical keratome. Additional methods or details of implanting the inlay can be found in, for example, U.S. patent application Ser. No. 11/293,644, filed Dec. 1, 2005 (Patent Application Pub. US 2007/0129797 A1) and U.S. patent application Ser. No. 11/421,597, filed Jun. 1, 2006 (Patent Application Pub. US 2007/0280994 A1), which are incorporated by reference herein.

Figure 2:
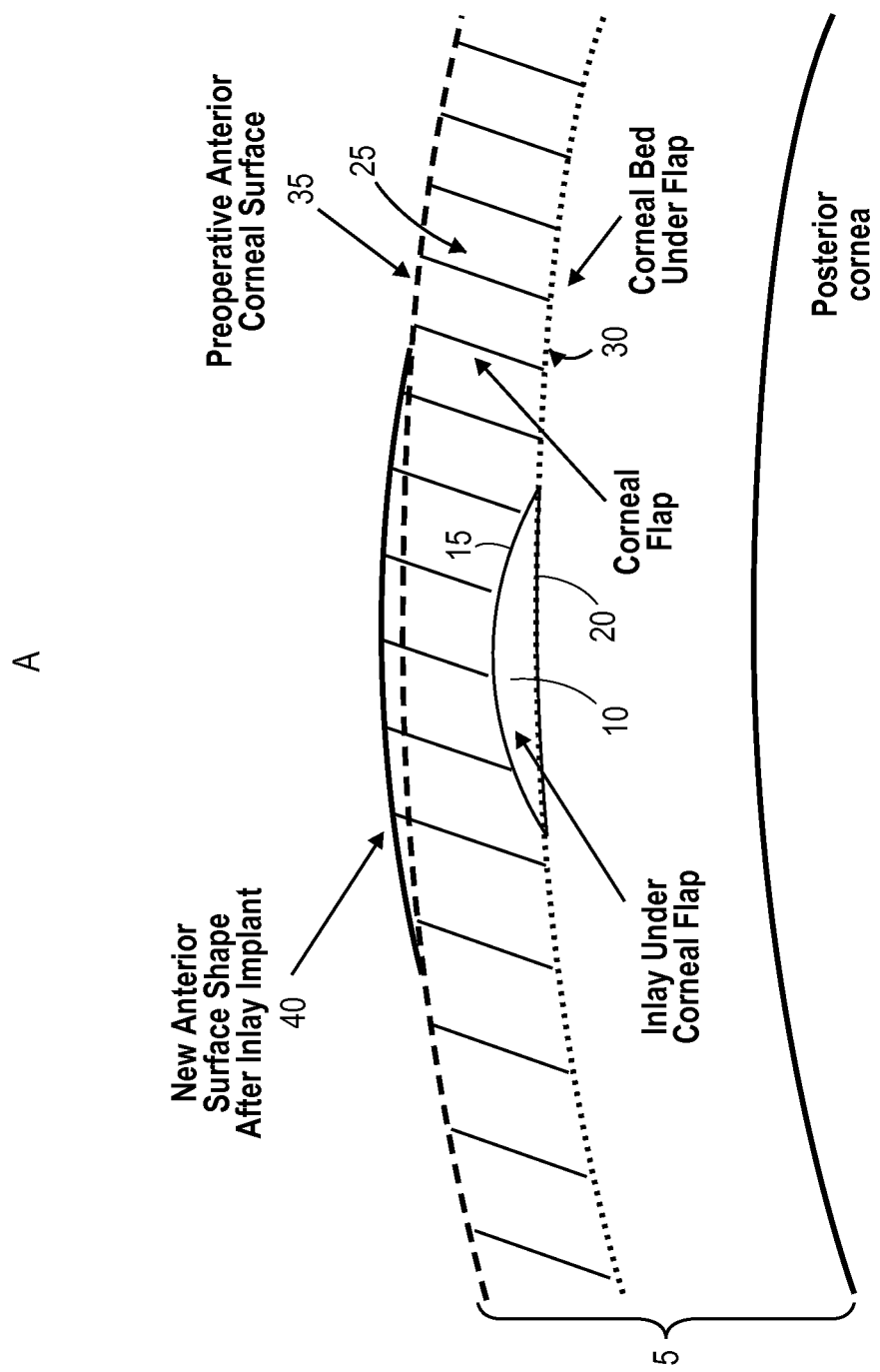
FIGS. 2 and 3 show an exemplary steepening of a central portion of the anterior surface of the cornea after an inlay has been implanted within the cornea.

As can be seen in FIG. 2, inlay 10, once implanted within the cornea, changes the refractive power of the cornea by altering the shape of the anterior surface of the cornea from pre-operative shape 35 (shown with dashed line) to post-operative shape 40 (shown as a solid line). In FIG. 2, the inlay changes the shape of a central portion of the anterior surface of the cornea, while a peripheral portion of the anterior surface peripheral to the central portion does not change shape. FIG. 2 shows an elevation change in the central portion of the anterior surface of the cornea. The elevation change includes a steepening of the central portion. The curvature of the central zone is increased to provide for near vision in the central portion, while the shape of the peripheral zone does not change and provides for distance vision peripheral to the central zone. The inlay in FIG. 2 can be used to correct for presbyopia because the central zone's increased curvature increases the eye's ability to focus on near objects.

In some embodiments the inlay has properties similar to those of the cornea (e.g., index of refraction around 1.376, water content of 78%, etc.), and may be made of hydrogel or other clear bio-compatible material. The inlay can be comprised of a variety of materials including, for example and without limitation, Lidofilcon A, Poly-HEMA (hydroxyethyl methylacrylate), poly sulfone, silicone hydrogel. In some embodiments the inlay comprises from about 20% to about 50% HEMA (hydroxyethyl methylacrylate), from about 30% to about 85% NVP (N-vinyl pyrrolidone), and/or about 0% to about 25% PVP (polyvinyl pyrrolidone). Other formulations of such materials cover compositions ranging from about 15% to about 50% MMA (methyl methylacrylate), from about 30% to about 85% NVP, and/or about 0% to about 25% PVP (polyvinyl pyrrolidone).

In some embodiments the water content of these compositions ranges from about 65% to about 80%. In one particular embodiment the inlay comprises about 78% NVP and about 22% MMA(methyl methacrylate), allymethacrylate as a crosslinker, and AIBN (azobisisobutylonitrile) as the initiator. Exemplary additional details and examples of the inlay material can be found in U.S. patent application Ser. No. 11/738,349, filed Apr. 20, 2007, (U.S. Patent Application No. US 2008/0262610 A1), which is incorporated by reference herein. In some embodiments the inlay has an index of refraction of approximately 1.376+/−0.0.008, which is substantially the same as the cornea. As a result, the inlay does not have intrinsic diopter power. The inlay can, however, have an index of refractive that is substantially different than the index of refraction of the cornea such that the inlay has intrinsic diopter power (in addition to changing the curvature of the anterior surface of the cornea). Exemplary details of a lens with intrinsic diopter power and methods of use, the features of which can be incorporated into the methods herein, are described in U.S. patent application Ser. No. 11/381,056, filed May 1, 2006 (Patent Application Pub. US 2007/0255401 A1), which is incorporated herein by reference.

Figure 3:
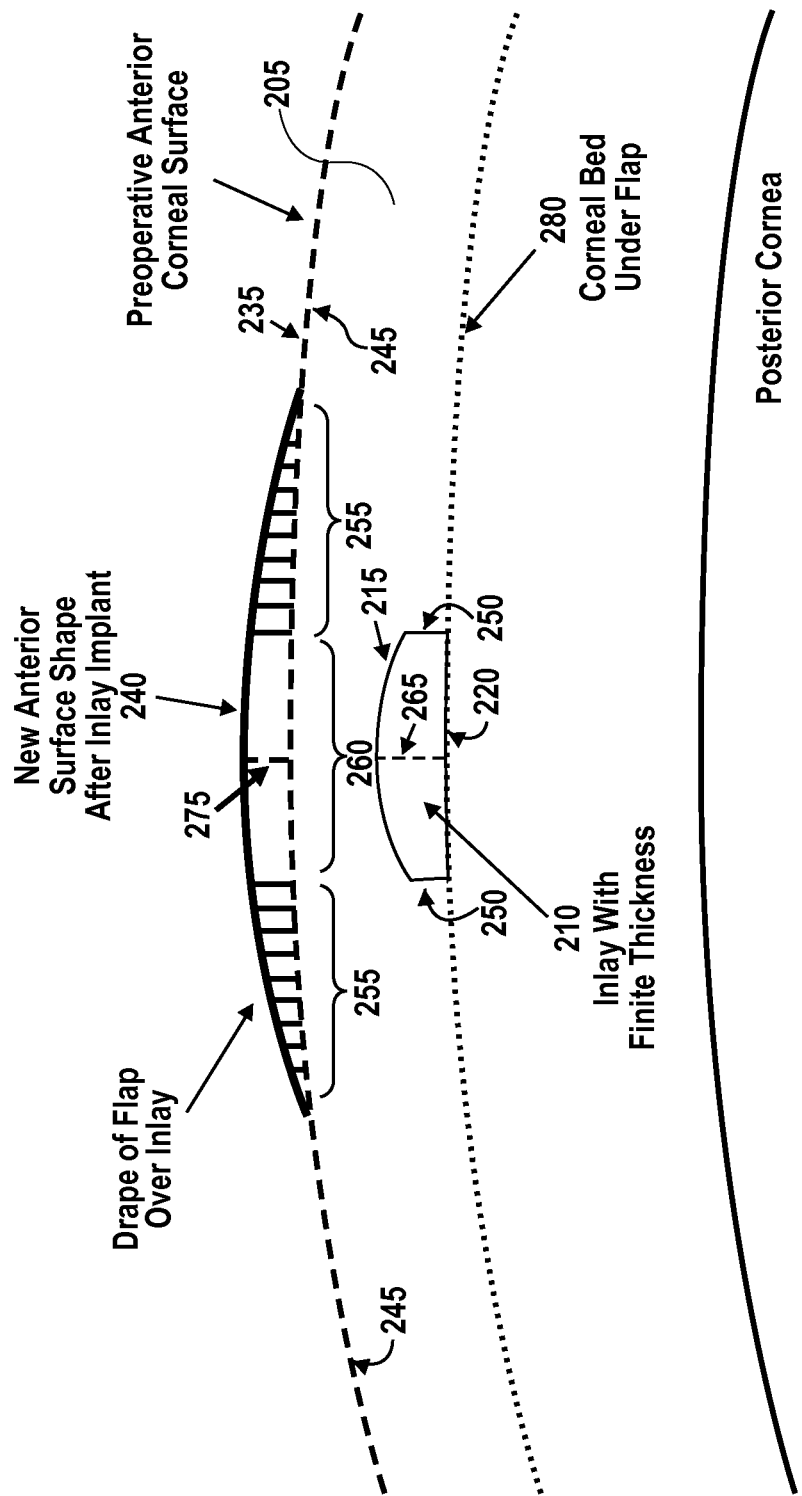

FIG. 3 illustrates a cross-sectional side view of an exemplary biomechanical effect of inlay 210 on the shape of the post-operative anterior corneal surface 240. Inlay 210 has center thickness 265, edge thickness 250, anterior surface 215, and posterior surface 220. The "effect" zone (which may also be referred to herein as "central zone"), or the region of the anterior surface whose curvature is altered due to the presence of the inlay, extends peripherally beyond the diameter of inlay 210. The "effect" zone comprises the geometric projection of the inlay diameter on the anterior surface 260 and "an outer effect zone" 255 peripheral to the projection of the inlay diameter. The effect zone has a center thickness 275.

Figure 4:
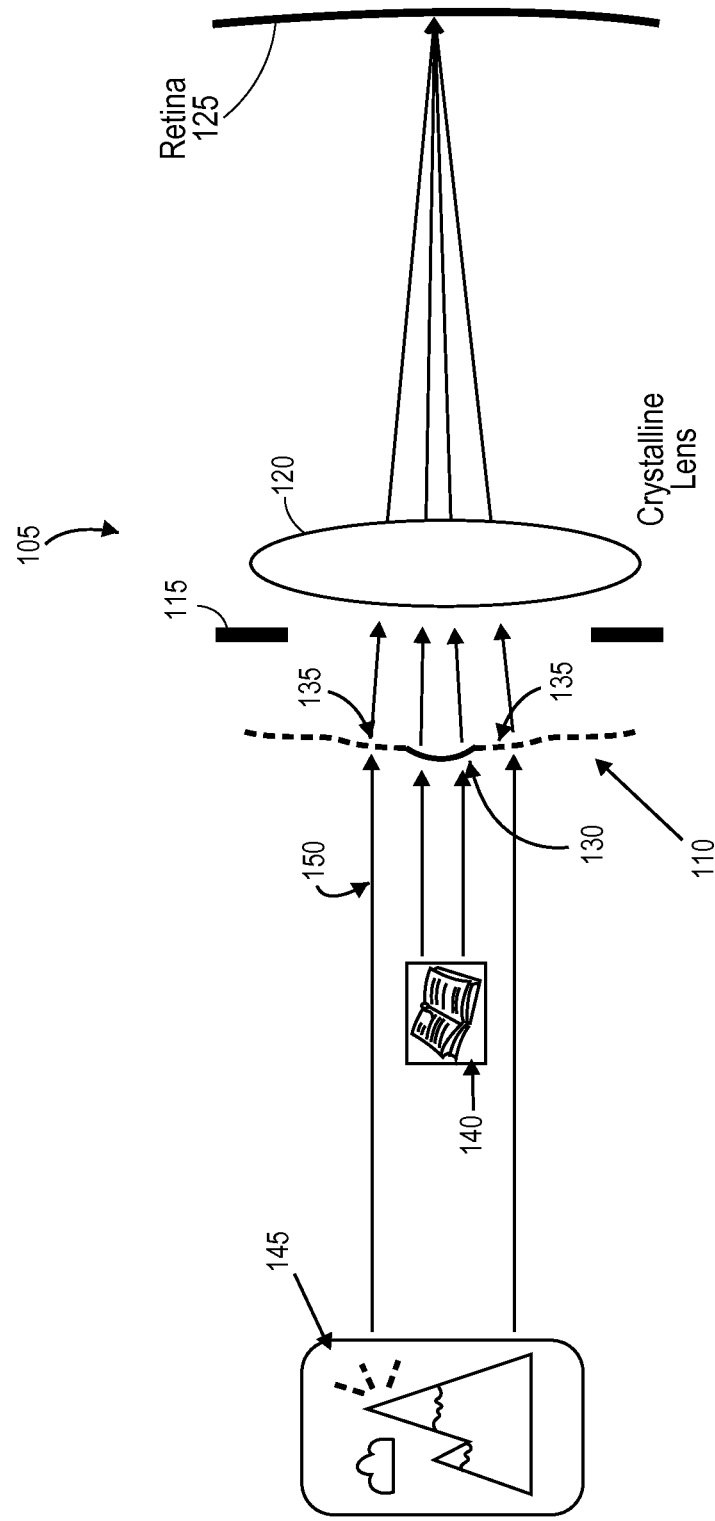
FIG. 4 illustrates how an inlay as described herein can be implanted within a cornea to provide center near vision and peripheral distance vision in an eye.

FIG. 4 illustrates an exemplary embodiment in which an inlay is used to provide near vision while providing distance vision to correct for presbyopia. The eye comprises cornea 110, pupil 115, crystalline lens 120, and retina 125. In FIG. 4, implanting the inlay (not shown) centrally in the cornea creates a small diameter "effect" zone 130 in the cornea. Both the inlay diameter and effect zone diameter are smaller than the pupil 115 diameter. The "effect" zone 130 provides near vision by increasing the curvature of the anterior corneal surface in a central region of the cornea, and therefore the diopter power of the "effect" zone 130. The region of the cornea peripheral to the "effect" zone 135 has a diameter less than the diameter of the pupil and provides distance vision. The subject's near vision is therefore improved while minimizing the loss of distance vision in the treated eye.

An exemplary advantage of this type of inlay is that when concentrating on nearby objects 140, the pupil naturally becomes smaller (e.g., near point miosis) making the inlay effect even more effective. Near vision can be further increased by increasing the illumination of a nearby object (e.g., turning up a reading light). Because the "effect" zone 130 is smaller than the diameter of pupil 115, light rays 150 from distant object(s) 145 by-pass the inlay and refract using the region of the cornea peripheral to the "effect" zone to create an image of the distant objects on the retina 125. This is particularly true with larger pupils. At night, when distance vision is most important, the pupil naturally becomes larger, thereby reducing the inlay effect and maximizing distance vision.

A subject's natural distance vision is in focus only if the subject is emmetropic (i.e., does not require correction for distance vision). Many subjects are ammetropic, requiring either myopic or hyperopic refractive correction. Especially for myopes, distance vision correction can be provided by myopic Laser in Situ Keratomileusis (LASIK) or other similar corneal refractive procedures. After the distance corrective procedure is completed, the small inlay can be implanted in the cornea to provide near vision. Since LASIK requires the creation of a flap, the inlay may be inserted concurrently with the LASIK procedure. The inlay may also be inserted into the cornea after the LASIK procedure as the flap can be re-opened. This type of inlay may therefore be used in conjunction with other refractive procedures, such as LASIK for correcting myopia or hyperopia.

In some embodiments (e.g., as shown in FIG. 4) an inlay is implanted to create an effect zone that is less than the pupil diameter and is used for correcting presbyopia. Presbyopia is generally characterized by a decrease in the ability of the eye to increase its power to focus on nearby objects due to, for example, a loss of elasticity in the crystalline lens over time. Typically, a person suffering from Presbyopia requires reading glasses to provide near vision. For early presbyopes (e.g., about 45 to 55 years of age), at least 1 diopter is typically required for near vision. For complete presbyopes (e.g., about 60 years of age or older), between 2 and 3 diopters of additional power is required. In an exemplary embodiment, a small inlay (e.g., about 1 to about 3 mm in diameter) is implanted centrally in the cornea to induce an "effect" zone on the anterior corneal surface (e.g., about 2 to about 4 mm in diameter) that is smaller than the optical zone of the cornea for providing near vision while also allowing distance vision in a region of the cornea peripheral to the effect zone.

The first step in correcting the vision of a subject by altering the cornea is generally determining the desired post-operative shape of the anterior corneal surface which will provide the desired refractive power change (i.e., determining the shape change for the anterior surface of the cornea). The shape of the desired anterior surface may be the result of a biomechanical response as well as epithelial remodeling of the anterior corneal surface as a result of the vision correction procedure. Corneal epithelial remodeling will be described in more detail below. Based on a biomechanical response and an epithelial response, the vision correction procedure is performed (e.g., implanting an inlay) to induce the desired anterior surface change.

This disclosure includes an exemplary method of determining a desired anterior corneal shape to provide for corrective vision. One particular embodiment in which the method includes implanting an inlay within the cornea to provide for center near and peripheral distance will be described. In some embodiments a central zone on the anterior corneal surface with a sharp transition is preferred (i.e., substantially without an outer effect zone which can be seen in FIG. 3). A sharp transition maximizes both the near and distance power efficiencies. In practice, the effects of epithelial remodeling typically prevent "sharp" transitions. Empirically, the anterior surface change induced by the inlay can be given by a symmetric polynomial of at least eighth order:

$$\text{Elev}(r)=a0+a2\times r^2+a4\times r^4+a6\times r^6+a8\times r^8 \qquad \text{Eq 1.}$$

Where "Elev" is the change in anterior corneal surface elevation due to the inlay, a0, a2, a4, a6 and a8 are the coefficients governing the shape And "r" is the radial extent location from the center of the anterior surface change.

The elevation change discussed herein is azimuthally symmetric in plane perpendicular to the axis of the cornea. But orthogonal asymmetries may be included with more complex inlay designs, attempting to correction of corneal astigmatism, pre-existing in the subject's eye. Physically, there are useful restrictions on the form of the elevation expression. At r=0, the elevation change is maximal and is central height "hctr". From the symmetry, at r=0, the first derivative of elevation expression must be zero. The extent of the inlay-induced change is limited to a maximal radius ($r_z$), where $\text{Elev}(r_z)$=0. And because the elevation smoothly transitions to the original cornea at $r_z$, the first derivative may also be zero; i.e., $d\text{Elev}(r_z)/dr$=0.

With these restrictions, the elevation change can be characterized by four independent parameters: hctr, $r_z$, a6 and a8. And the remaining coefficients are given by:

$$a0=hctr$$

$$a2=2*\text{alpha}/r_z{}^2-\text{beta}/2/r_z$$

$$a4=\text{beta}/2/r_z{}^3-\text{alpha}/r_z{}^4$$

Where:

alpha=−hctr−a6*rz^6−a8*rz^8 beta=−6*a6*rz^5−8*a8*rz^7

Thus, the ideal anterior corneal elevation change can be expressed by four independent parameters: hctr, $r_z$, a6 and a8.

Table 1 provides ideal anterior corneal surface changes for three spectacle ADD powers (1.5 diopters, 2.0 diopters, and 2.5 diopters) and for three pupil sizes (small, nominal and large) when using near vision.

TABLE 1

Examples of Ideal Anterior Corneal Surface Change Designs

| Design Type (mm) | Pupil Size | ADD (diopters) | "hctr" (microns) | rad zone (mm) | a6 (mm$^{-5}$) | a8 (mm$^{-7}$) |
|---|---|---|---|---|---|---|
| MaxN @ 2.5 | small | 1.5 | 4.30 | 1.39 | −4.500E−04 | 2.800E−04 |
| MaxN @ 3.0 | nominal | 1.5 | 5.06 | 1.50 | −2.830E−04 | 1.466E−04 |
| MaxN @ 3.5 | large | 1.5 | 6.24 | 1.66 | −3.374E−04 | 9.972E−05 |
| MaxN @ 2.5 | small | 2.0 | 5.38 | 1.36 | −2.450E−03 | 8.100E−04 |
| MaxN @ 3.0 | nominal | 2.0 | 7.15 | 1.55 | −1.830E−03 | 4.420E−04 |
| MaxN @ 3.5 | large | 2.0 | 10.70 | 1.87 | −6.014E−04 | 1.108E−04 |
| MaxN @ 2.5 | small | 2.5 | 6.58 | 1.38 | −2.247E−03 | 7.904E−04 |
| MaxN @ 3.0 | nominal | 2.5 | 9.87 | 1.68 | −7.639E−04 | 1.950E−04 |
| MaxN @ 3.5 | large | 2.5 | 13.70 | 1.97 | −3.658E−04 | 7.109E−05 |

Performing the optical ray-trace optimization to derive the optimal anterior corneal elevation change (Elev) requires a model eye which mimics the key optical functions of the human eye. The finite eye model by Navarro (Accommodation dependent model of the human eye with aspherics, R. Navarro. et al., JOSA Vol 2 No 8 1985 p. 1273-1281) provides one such model. For these design purposes, the Navarro provides anatomically correct values for the corneal physical and optical properties and provides total eye properties such as normal values for the total eye spherical aberrations, chromatic aberration and Stiles-Crawford effect. Other model eyes can be also used if they specify these criteria.

To include the anterior corneal elevation change (Elev) in the Navarro eye model, the Elev surface is added to the anterior surface of the Navarro eye model. Calculations of the image quality created by the anterior surface change to the eye model are accomplished using any of many commercial ray-trace software packages. For the examples provided, the Zemax-EE Optical Design Program (2008) from the Zemax Development Corporation was used.

The objective of the ray-trace optimization is to find the elevation surface parameters (hctr, $r_z$, a6 and a8) that maximize the optical performance for a given set of assumptions. There are many optical metrics of image quality used in optical design. Of these, the Modulation Transfer Function (MTF) is particularly useful for optical designs, simultaneously using two zones of optical power. The MTF is the efficiency of transferring the contrast of the original object to the contrast of the image of the object on the human retina. The MTF efficiency (modulation) is plotted as a function of the spatial frequency information in the image of the object. The spatial frequency can be thought of as one divided by the size of features in the image. Thus, large spatial frequencies represent very fine features in the image, and low spatial frequencies represent very large features in the image. The image quality is maximized when the MTF values at selected spatial frequencies have their highest values.

The assumptions are derived from the inlay's design requirement to provide a good distance image from light rays passing through the peripheral region between the pupil diameter and the inlay's effect zone ($r_z$), and a good near image for light rays passing through the central effect zone. Thus, the ray-trace program is set with at least two configurations. In the first, the object for the eye model is set to infinity (e.g., looking at a distant object). In the second configuration, the object is set at a near distance. The typical distance of near work and ophthalmic prescription is 40 cm, which corresponds to a spectacle ADD of 2.5 diopters.

For each configuration, the model eye's pupil size must be set. Of the many choices, two are the most logical. In the first, the pupil size is set the same for both configurations and goal of the optimization is to find the elevation parameters which give equal distance and near image quality. The second choice is to set separate pupil sizes for the distance and near configurations. The near configuration pupil size is set to subject's pupil size in a well illuminated setting i.e., the peripheral distance zone is effectively zero. This condition provides the maximal near distance capability. The distance configuration pupil size is set to the subject's night-time or dim-light pupil size, where distance vision is maximized. For the examples provided herein, the latter method was used, using different pupil sizes for the distance and near configurations. Note that regardless of the method chosen, the same range of ideal elevation profiles (e.g., Table 1) will be found.

The human pupil size varies for a given set of illumination conditions, with two important trends. As an individual ages, the nighttime pupil size decreases. Additionally, when looking at a near object, the pupil diameter reduces by about 0.5 mm. Based on literature and clinical experience, the near configuration pupil in bright lighting is considered "small" if approximately 2.5 mm in diameter, "nominal" if approximately 3.0 mm, and "large" if approximately 3.5 mm in diameter. For the distance configuration, the nighttime pupil sizes vary greatly, and any loss of distance vision is compensated for by the fellow eye. Thus, one nighttime pupil size is sufficient for design purposes and a diameter of 5.0 mm is suggested by the literature/clinical experience.

The optimization tools of the ray-trace software program are now utilized. The elevation parameters (hctr, $r_z$, a6 and a8) are varied until the MTF of the near configuration is maximized while simultaneously maximizing the MTF of the distance configuration. The ideal design is clearly a function of the assumed pupil sizes. In practice, subject may be screened preoperatively, allowing the surgeon to select the inlay design most appropriate for the subject's pupil size range and desired visual outcome.

In this particular method of implanting an inlay, once the desired anterior surface change has been determined, the inlay to be implanted is selected, taking into account and compensating for a biomechanical response and an epithelial response due to the presence of the inlay. Exemplary biomechanical interactions which can be taken into consideration can be found in U.S. patent application Ser. No. 11/738,349, filed Apr. 20, 2007, to which this application claims priority and which is incorporated by reference herein.

Empirical data presented herein below provides details of some aspects of a biomechanical response and an epithelial response due to the presence of an intracorneal inlay.

Figure 5:
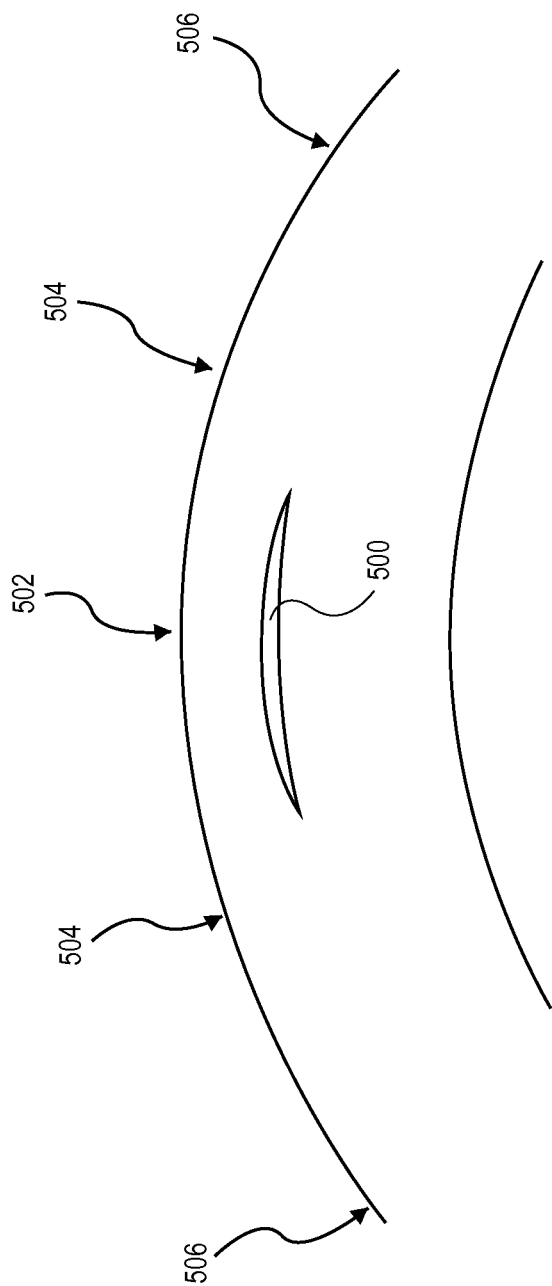
FIG. 5 illustrates the locations of epithelial thinning and thickening after an inlay has been implanted within a cornea.

Petroll et al. noted that intracorneal inlays induced epithelial thinning of the epithelium overlying the inlay. FIG. 5 illustrates a cross-section side view of inlay 500 positioned within the cornea stroma layer. Imaging a portion of the cornea with optical coherence tomography (OCT) has shown that after an inlay is positioned within the cornea, the epithelial layer attempts to reduce an induced change in shape in the anterior surface of the cornea. There has been a noticed epithelial thinning 502 radially above the inlay, and an epithelial thickening 504 at locations slightly beyond the diameter of the inlay. The epithelial layer remains unchanged in outer region 506. This epithelial remodeling appears to be a natural response by the epithelial layer to smooth out, or reduce, the induced increase in curvature of the anterior surface of the cornea. By thinning in region 502 and thickening in region 504, the epithelium remodels and attempts to return the anterior surface to its pre-operative shape. Epithelial remodeling in this context is the epithelial layer's way of attempting to reduce the change induced by the implantation of a foreign object within the cornea. The thinning and thickening have each been observed to be about 10 microns.

This epithelial remodeling will adjust the shape of the anterior surface of the cornea after the inlay has been implanted. This will adjust the refractive effect of the inlay. In the examples described above, epithelial remodeling will attempt to reduce an induced steepening in curvature of the central effected zone by thinning a central region of the epithelium and thickening a peripheral portion of the epithelium. Understanding the epithelial remodeling is therefore important to understand how an inlay will ultimately change the shape of the anterior surface of the cornea. In some embodiments, therefore, selecting an inlay to be implanted within the cornea to be used for center near vision comprises selecting an inlay that will compensate for epithelial remodeling and still cause the anterior surface of the cornea to adjust to the desired shape. Huang et al. describes the effects of epithelial remodeling as it relates to ablation of cornea tissue (i.e., removal of tissue). Huang, however, fails to address an epithelial remodeling after the addition of material to the cornea, such as an intracorneal inlay. An embodiment herein focuses on the epithelial remodeling after the addition of material to the cornea.

Figure 6:
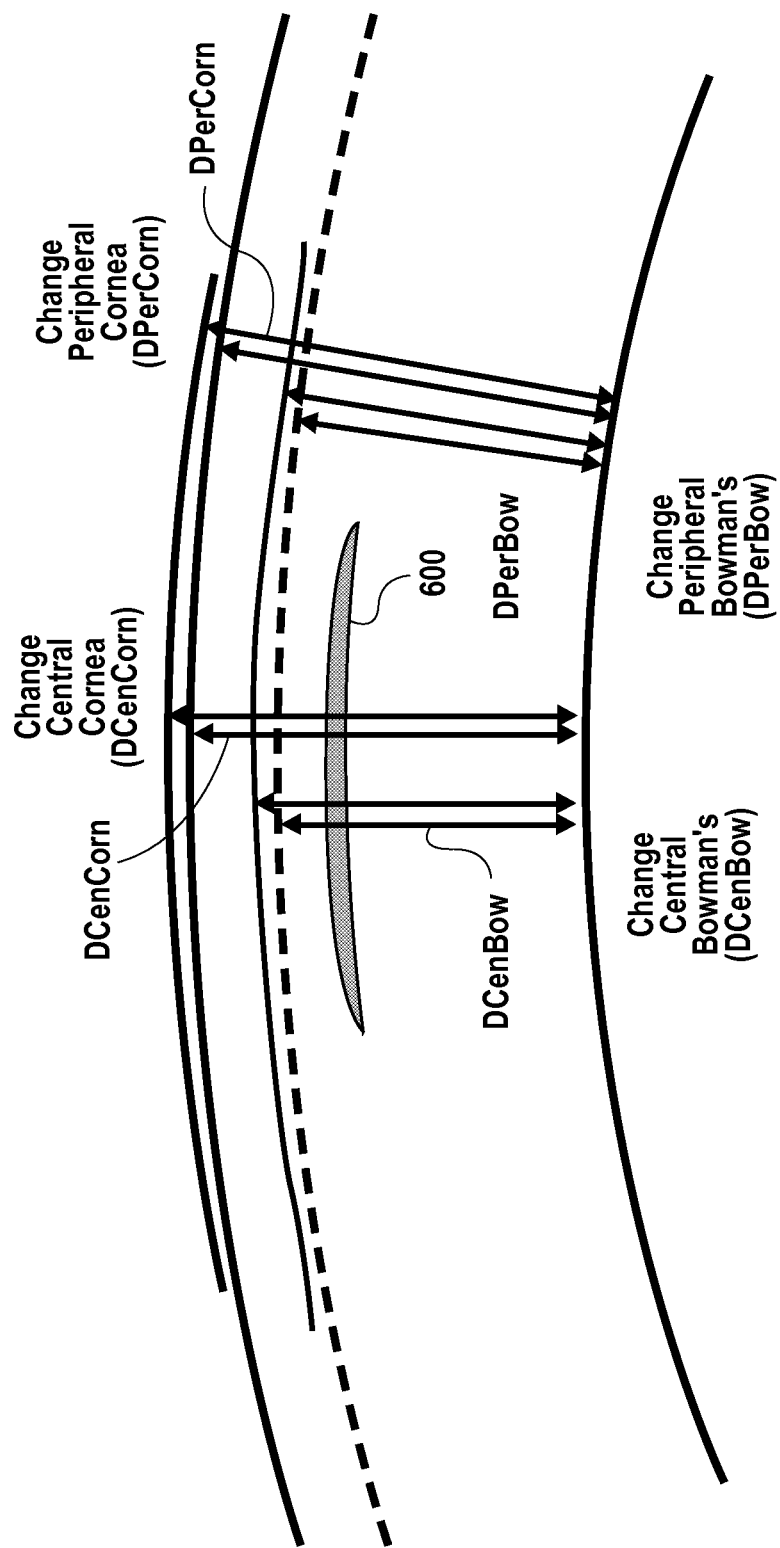
FIG. 6 illustrates the shape change of Bowman's layer and the anterior surface of the cornea in response to an inlay being implanted within the cornea.

FIG. 6 illustrates a cross-sectional side view of a portion of a cornea before and after implantation of an intracorneal inlay 600. The change in the central region of Bowman's layer "DCenBow" is shown by the difference in the two arrows. Similarly, the changes in a peripheral region of Bowmans' layer "DPerBow", the central anterior surface of cornea "DCenCor", and a peripheral region of the anterior surface of cornea "DPerCorn" are represented.

Figure 8:
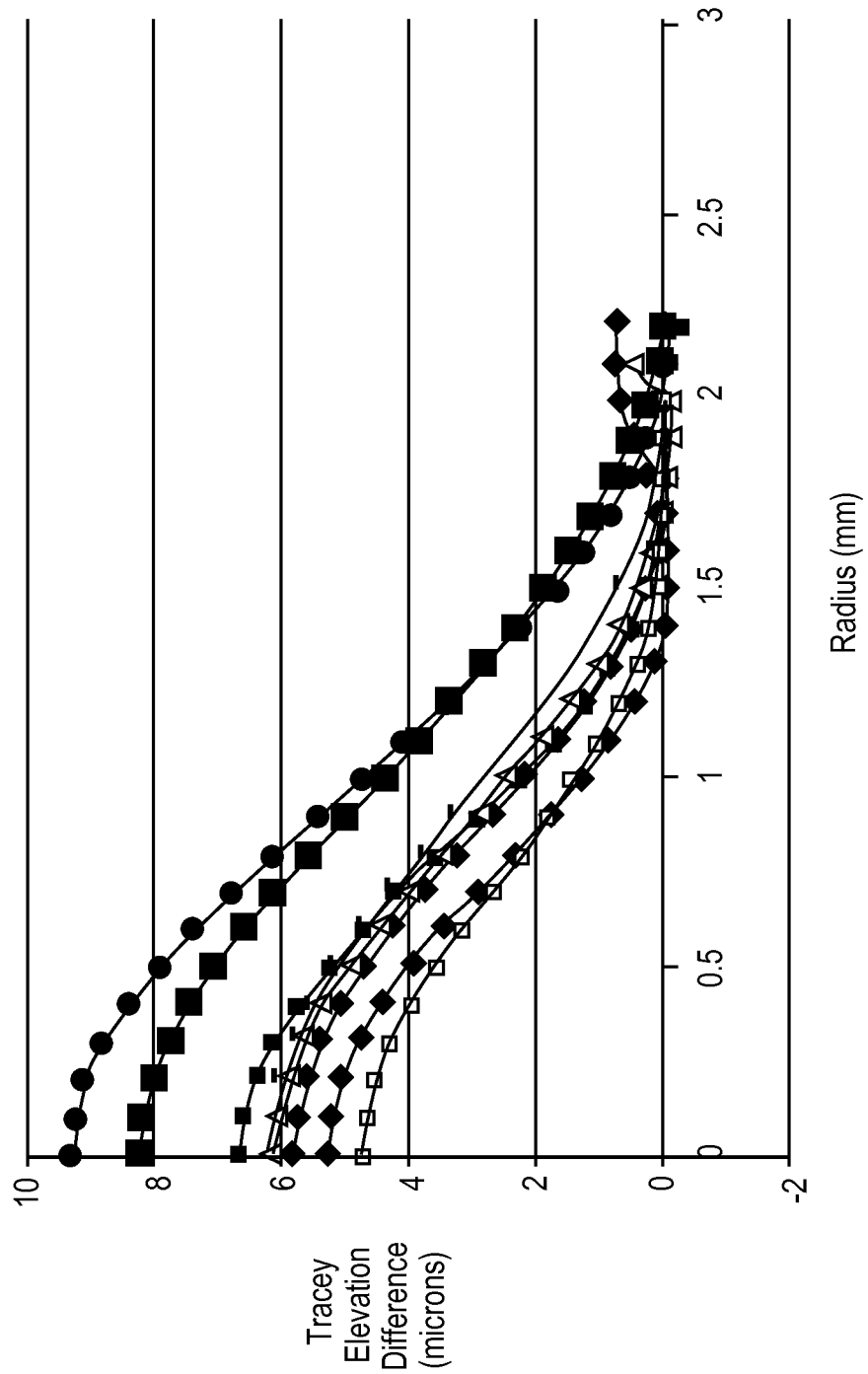
FIGS. 8 and 10 chart the changes in elevation of the anterior surface of the cornea (i.e., the difference in elevation between pre-op and post-op) versus the radius of the anterior surface of the cornea for patients in which an inlay was implanted.

FIG. 7 presents clinical data (e.g., distance and near visual acuity and the refractive effect created by the inlay) and the change in anterior corneal surface elevation derived from pre-op and post-op wavefront measurements of nine patients in whom a 1.5 mm diameter inlay with an average center thickness of about 32 microns (ranging from 30 microns to 33 microns) was implanted. The "Postop ucnVA" column shows the post-operative uncorrected near visual acuity. The second "PostuncNL" column shows the lines of uncorrected near visual acuity change (positive represents a gain while negative represents a loss). The "PostOp ucDVA" column shows the post-operative uncorrected distance visual acuity. The "PostucDL" column shows the lines of uncorrected distance visual acuity change (positive represents a gain while negative represents a loss). The "InlayADDeff" column shows the refractive effect of the inlay calculated from clinical refraction data. The "InlayCen2.5 mmSph" column shows the refractive effect of the inlay, centered on the inlay for a 2.5 mm diameter pupil, calculated from Tracey wavefront data. The "Diff Fit Ht" column shows the central anterior corneal elevation change (i.e., the difference between post-op and pre-op) calculated from Tracey wavefront data. The "Diff Eff Dia" column shows the effect zone diameter. FIG. 8 charts the changes in elevation of the anterior surface of the cornea (i.e., the difference in elevation between pre-op and post-op) versus the radius of the anterior surface of the cornea for the nine patients in whom the 1.5 mm diameter inlay was implanted.

Figure 10:
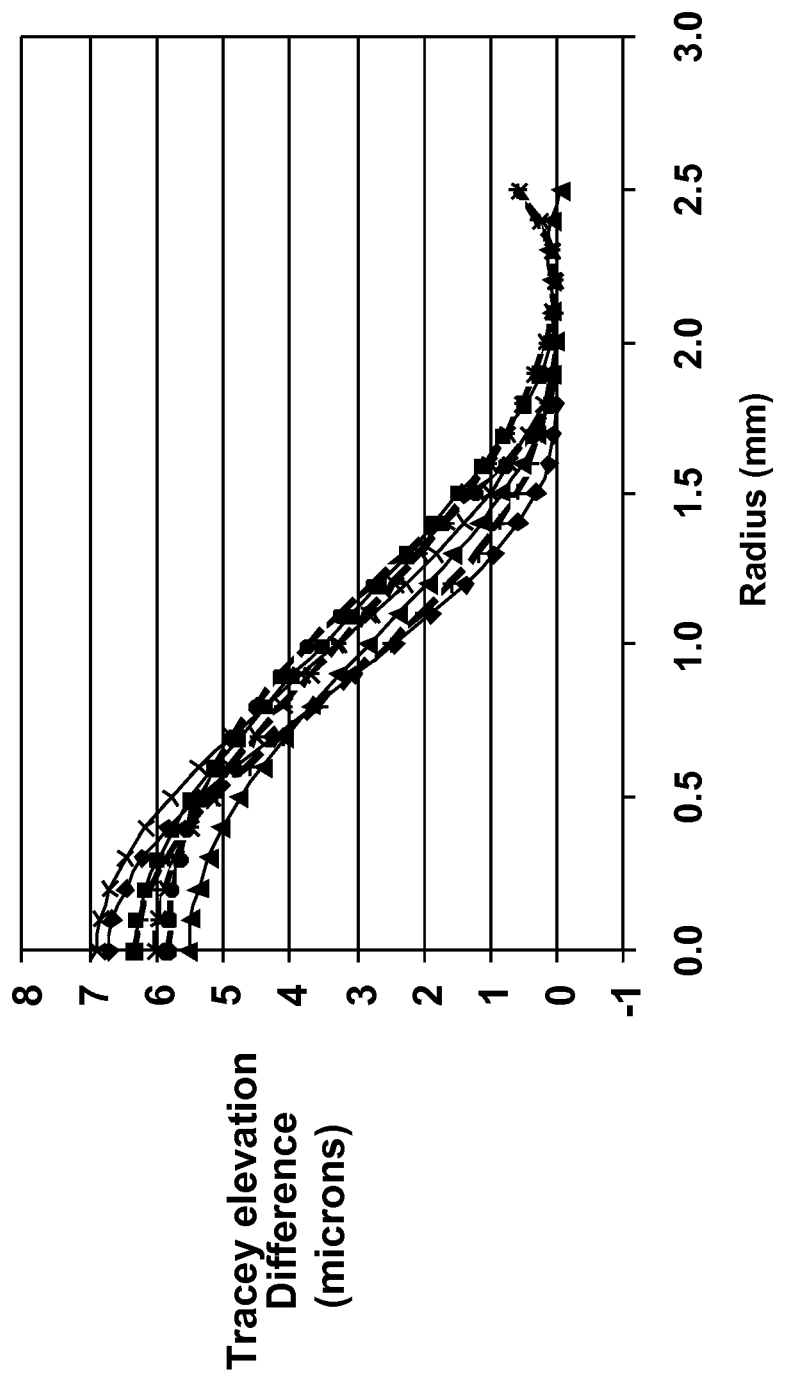

FIG. 9 presents clinical data the change in anterior corneal surface elevation derived from pre-op and post-op wavefront measurements of seven patients in whom a 2.0 mm diameter inlay with an average center thickness of about 32 microns (ranging from 31 microns to 33 microns) was implanted. The column headings are the same as those shown in FIG. 8. FIG. 10 charts the changes in elevation of the anterior surface of the cornea (i.e., the difference in elevation between pre-op and post-op) versus the radius of the anterior surface of the cornea for the seven patients in whom the 2.0 mm diameter inlay was implanted.

As shown in the data there is patient-to-patient variability with respect to the epithelial remodeling of the cornea. The designs and methods described herein, however, show effectiveness despite this variability.

A merely exemplary method for designing or selecting an implantable cornea device such as a small inlay to provide for central near vision and peripheral distance visions, which also compensates for epithelial remodeling or other physiological responses to the inlay will now be given. One step in the method is determining a maximum effect zone diameter ($d_{eff}$) that is an acceptable tradeoff between the near vision improvement and the loss of distance vision. Considerations include the pupil size of the specific subject or a group of characteristic subjects (e.g., subjects within a particular age range) while reading or viewing nearby objects, and the pupil size for distance viewing, especially at night. Based on the analysis of pupil sizes recorded in subjects with various intracorneal inlays, consideration of the distance and near visual acuities, review of literature on pupil size changes, and supplemental theoretical ray-trace analysis of theoretical eyes with the intracorneal inlay, in some embodiments the desired effect zone diameter is between about 2.0 mm and about 4.0 mm. In an exemplary application, the inlay is placed in one eye to provide near vision while distance correction by other means is performed on both the inlay eye and the fellow eye. In this example, both eyes contribute to distance vision, with the non-inlay eye providing the sharpest distance vision. The eye with the inlay provides near vision.

An additional step in the method is to determine the inlay diameter. As shown above, the "effect" zone increases with inlay diameter. Based on empirical data discussed above in FIG. 7 regarding implanting an inlay with a diameter of 1.5 mm, the inlay can be selected to have a diameter between about 1.5 mm and about 2.9 mm less than the diameter of the desired effect zone diameter. Excluding the 3.0 mm effect zone diameter from patient 7, the inlay can be selected to have a diameter between about 2.2 mm and 2.9 mm less than the diameter of the desired effect zone diameter. Based on the average effect zone diameter of 3.9 mm from all nine patients, in some embodiments the inlay is selected to have a diameter of about 2.4 mm less than the effect zone diameter.

Based on empirical data discussed above in FIG. 9 regarding implanting an inlay with a diameter of 2.0 mm, the inlay can be selected to have a diameter between about 1.6 mm and about 2.4 mm less than the diameter of the desired effect zone diameter. In some embodiments the inlay can be selected to have a diameter between about 1.8 mm and about 2.4 mm less than the diameter of the desired effect zone diameter. Based on the average effect zone diameter of 4.0 mm from all seven patients, in some embodiments the inlay is selected to have a diameter of about 2.0 mm less than the effect zone diameter. In this manner an inlay diameter can be selected which compensates for epithelial remodeling.

An additional step is to determine the inlay's posterior radius of curvature. The inlay is positioned on a lamellar bed, which is the anterior aspect of the cornea underneath the flap (in embodiments in which a flap is created). The posterior curvature of the inlay should match the curvature of the lamellar bed to prevent diffuse material from filling in gaps between the inlay and the lamellar bed, which can lead to optical opacities. For inlays which are "stiffer" (i.e., greater modulus of elasticity) than the cornea, pre-operative estimates of the bed curvature are used to select the inlay with the appropriate posterior curvature. In the preferred embodiment, the inlay is more flexible (i.e., modulus of elasticity less than or equal to about 1.0 MPa) than the cornea (corneal modulus about 1.8 MPa), and the inlay will bend and conform to the bed curvature when placed under the flap. Analysis of the posterior shape of the implanted inlays by means of Optical Coherence Topography suggests that bed radius of curvature ranges between 6 mm and 9 mm. To avoid any possibility of a gap beneath the inlay, in some embodiments the posterior radius of curvature is about 10 mm.

An additional optional step is to determine the inlay edge thickness. A finite edge thickness 16 (see FIG. 1) creates a gap under the flap at the peripheral edge of the inlay, potentially leading to biochemical changes resulting in opacities in the cornea. Thus, in some embodiments the edge thickness is minimized and preferably is less than about 20 microns. In some embodiments the edge thickness is less than about 15 microns.

An additional step is determining the inlay center thickness (see "T" in FIG. 1). Based on the clinical data above shown in FIG. 7 in which a 1.5 mm diameter inlay is implanted (average center thickness of about 32 microns), the inlay center thickness is selected to be between about 3.0 and about 7 times the desired central anterior elevation change. Based on the average of 6.6 microns in central anterior elevation change, in one particular embodiment the inlay center thickness is determined to be about 5 times the desired central anterior elevation change. This data therefore shows a factor of about 5 for the inlays with a diameter of 1.5 mm.

Based on the clinical data above shown in FIG. 9 in which a 2.0 mm diameter inlay is implanted (average center thickness of about 32 microns), the inlay center thickness is selected to be between about 4.5 and about 6.0 times the desired central anterior elevation change. Based on the average of 6.2 microns in central anterior elevation change, in one particular embodiment the inlay center thickness is determined to be about 5 times the desired central anterior elevation change. This data therefore shows a factor of about 5 for the inlays with a diameter of 2.0 mm.

An additional step is determining the inlay anterior radius of curvature. The inlay's anterior surface shape and curvature influence the shape and curvature of the portion of the cornea's anterior surface above the inlay and the outer effect zone. A range of anterior radii of curvatures, based on empirical evidence (some of which can be found in U.S. patent application Ser. No. 11/738,349, filed Apr. 20, 2007, (U.S. Patent Application No. US 2008/0262610 A1, which is incorporated herein by reference) is between about 5.0 mm and about 10.0 mm. In some embodiments the selected anterior radius of curvature is between about 6 mm and about 9 mm. In particular embodiments the anterior radius of curvature is about 7.7 mm or about 8.5 mm. While spherical anterior and posterior surfaces have been described herein, non-spherical surfaces may be desirable. Such aspheric anterior inlay surfaces may be either flatter or steeper compared to a spherical surface.

An optional additional step is to determine an optional edge taper or bevel. Exemplary bevels are described in detail in U.S. patent application Ser. No. 11/106,983, filed Apr. 15, 2005 (Patent Application Pub. US 2005/0246016 A1), the disclosure of which is incorporated by reference herein. The shape of the bevel and the curvature of the anterior surface affect how fast the anterior surface outer effect zone returns to the original anterior corneal surface and influences the anterior corneal surface's outer effect zone shape. The outer effect zone shape in turn determines the distribution of dioptic powers in the outer effect zone region and the retinal image quality for primarily intermediate and near objects. The subtleties of the taper zone shape become most important when a sophisticated biomechanical model of the inlay and corneal interaction has been derived.

The above method is merely exemplary and not all of the steps need be included in selecting inlay parameters. For example, the inlay need not have a bevel and therefore selecting a bevel length or shape need not be performed when selecting an inlay profile to compensate for epithelial remodeling.

While portions of the disclosure above have highlighted selecting an inlay with specific features to compensate for an epithelial response, this disclose also includes methods of compensating for an epithelial response from a variety of other vision correcting intracorneal procedures. The discussion herein focuses on procedures that alter the stroma layer and for which the epithelial layer remodels to reduce the effect of the intracorneal procedure. One category of vision correction procedures that alter the stroma are procedures which remodel the cornea tissue. For example, corneal ablation procedures such as LASIK are included in this category. Remodeling the corneal tissue can be done with lasers, such as ultraviolet and shorter wavelength lasers. These lasers are commonly known as excimer lasers which are powerful sources of pulsed ultraviolet radiation. The active medium of these lasers are composed of the noble gases such as argon, krypton and xenon, as well as the halogen gases such as fluorine and chlorine. Under electrical discharge, these gases react to build excimer. The stimulated emission of the excimer produces photons in the ultraviolet region.

Procedures that alter the stroma layer also include procedures that weaken corneal tissue without ablating the tissue. 20/10 Perfect Vision has developed the intraCOR® treatment, for example, an intrastromal correction of presbyopia using a femtosecond laser. Procedures that introduce a foreign body or matter into the cornea, such as an inlay, are also included in this category. It is also contemplated that a flowable media, such as a fluid or uncured polymeric composition, could be positioned within the cornea as well to be used to correct vision.

These additional cornea procedures will provoke an epithelial response which in some embodiments is compensated for when performing the procedures. For example, corneal ablation procedures remove corneal tissue which changes the curvature of the anterior surface of the cornea. The epithelial layer then remodels to try and reduce the shape change. Performing the procedure to compensate for this epithelial remodeling will therefore allow the procedure to produce the desired change to the cornea.

Figure 11:
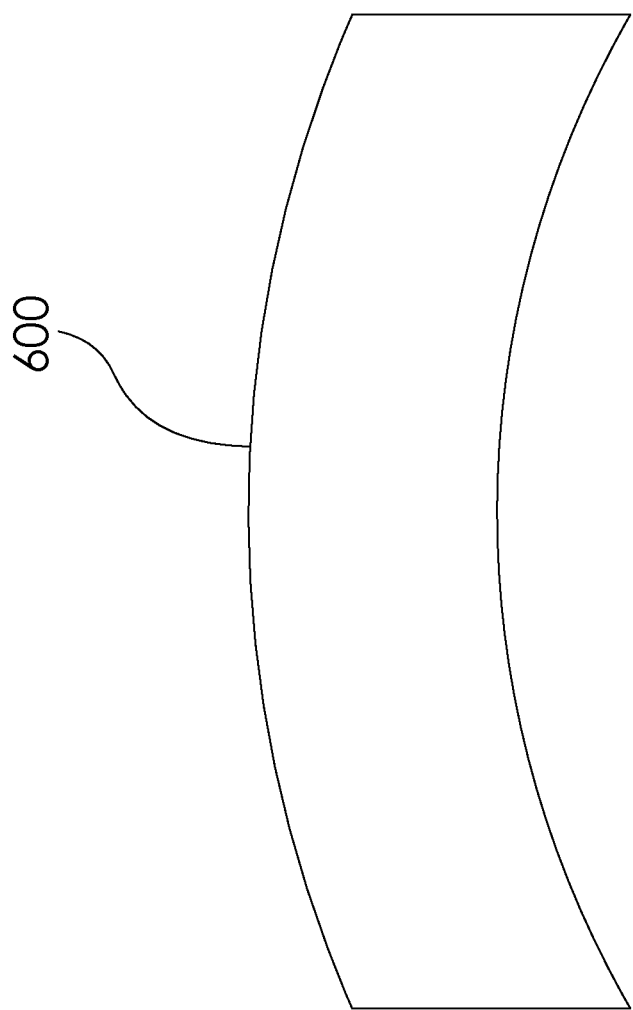
FIGS. 11-13 illustrate an exemplary method of lenticule extraction that corrects for presbyopia and accounts for epithelial remodeling.
Figure 12:
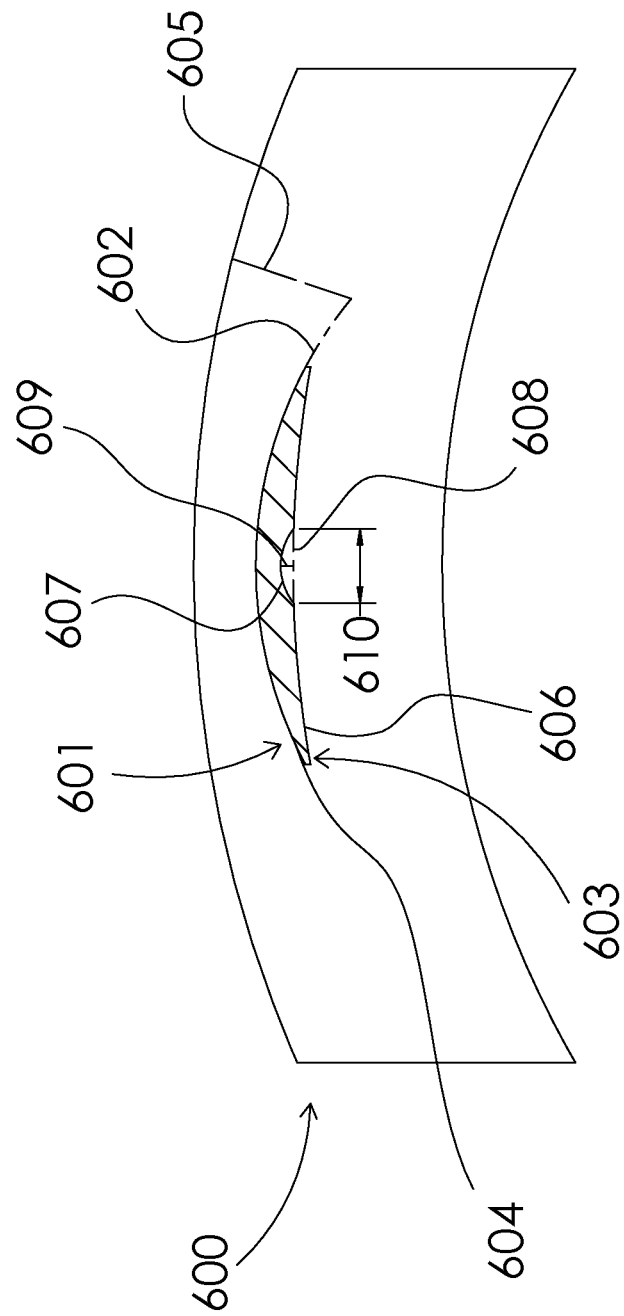
Figure 13:
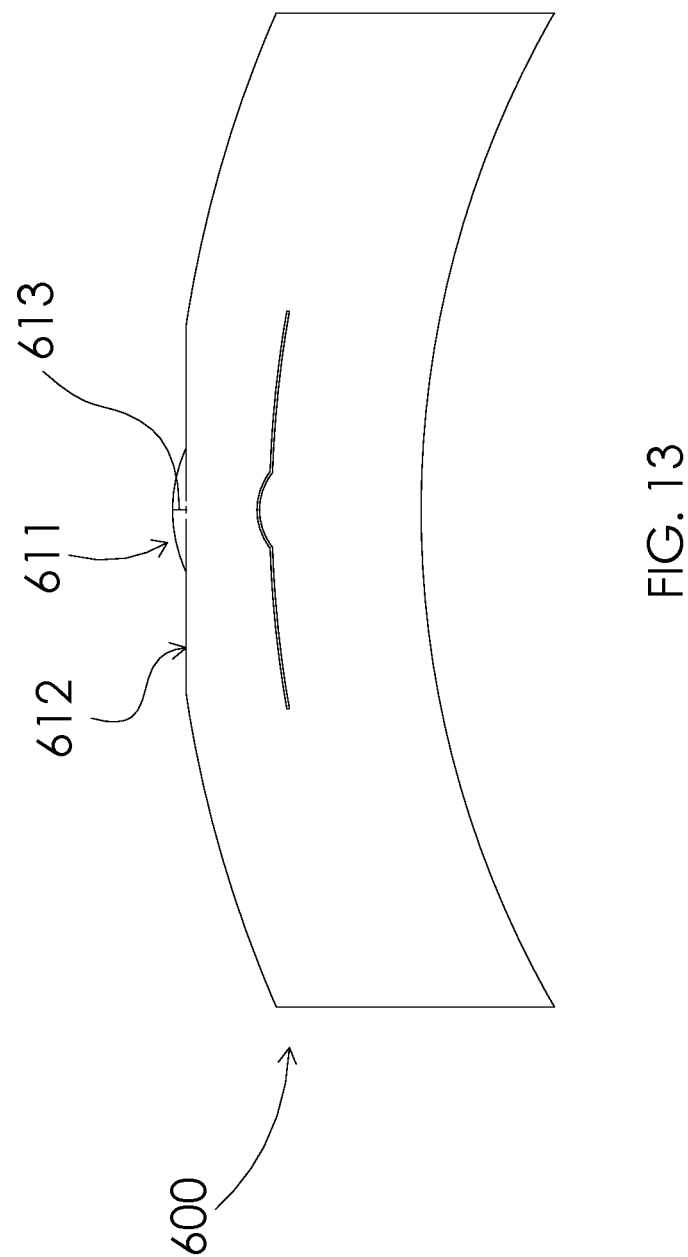

FIGS. 11-13 illustrate an additional exemplary method of correcting vision that uses a laser to remodel cornea tissue to induce a shape change in the anterior surface of the cornea. Just as in the embodiments above, FIGS. 11-13 illustrate a method of correcting for presbyopia that takes epithelial remodeling into consideration. In the method of FIGS. 11-13, a lenticule is created in the stroma and then removed to induce a shape change to the anterior surface of the cornea. General methods of lenticule creation and extraction, any of which can be used in any of the methods herein, can be found in the following U.S. Publications, the complete disclosures of which are incorporated by reference herein: 2010/0331831 to Bischoff et al., published on December 2010; 2014/0128855 to Wottke et al., published May 8, 2014; and 2014/0288540 to Bischoff et al., published Sep. 25, 2014. Lenticule extraction methods therein are commonly referred to as the "FLEx" and "SMILE" procedures. The procedures use a short-pulse laser, such as a femtosecond laser, to create an incision geometry in the cornea, separating a cornea volume (so-called "lenticule") in the cornea. Rather than ablating corneal tissue, both methods rely on lenticule creation and extraction. An exemplary advantage of these methods is that the quality of the incision is further improved by using a short pulse laser, such as a femtosecond laser. Additionally, only a single treatment device is needed; an excimer laser is not needed.

In the FLEx procedures, the lenticule is removed manually by the surgeon after the flap covering the lenticule has been folded back. A refinement of the FLEx method is referred to as the "SMILE" (Small Incision Lenticule Extraction) method in which no flap is created but rather only a small opening incision that serves to access the lenticule located beneath the so-called cap. The separated lenticule is removed through this small opening incision, as a result of which the biomechanical integrity of the anterior cornea is less affected than in a LASIK, FLEx or PRK (photorefractive keratectomy) procedure. Moreover, in this manner, fewer superficial nerve fibers in the cornea are cut and this has been proven to be advantageous when it comes to the restoration of the original sensitivity of the surface of the cornea. As a result, the symptom of dry eyes that often has to be treated after a LASIK procedure is often less severe and less protracted. Other complications after LASIK, which usually have to do with the flap (e.g., folds, epithelial ingrowth in the flap bed) occur less often in procedures without a flap.

The methods of lenticule creation and extraction described in the three patent application publications above are expressly incorporated by reference herein. In some of the methods described, lenticule creation and extraction can be used to treat myopia by removing the lenticule, which flattens the anterior surface of the cornea. For example, U.S. Publication 2014/0128855, in FIGS. 6A-7B, illustrates two exemplary methods of lenticule creation and extraction.

FIGS. 11-13 illustrate a method of lenticular extraction that corrects for presbyopia as well as treating myopia, although the methods herein can be used for other vision correction procedures.

FIG. 11 illustrates a portion of cornea 600 before the procedure has begun. FIG. 12 illustrates cornea 600 after lenticule 601 (shown in hashed lines) has been created with a femtosecond laser. Creating lenticule 601 includes creating anterior lenticule incision 602, posterior lenticule incision 603 (with a solid line), lenticule edge incision 604, and opening incision 605. Posterior lenticule incision 603 includes a peripheral region 606 and a central region 607. As shown, central region 607 of the posterior lenticule incision has an increased curvature relative to peripheral region 606. Central region 607 of posterior lenticule incision 603 increases the curvature of a central portion of the anterior surface of the cornea relative to a peripheral portion of the anterior surface of the cornea to correct for presbyopia, as is described herein. In this exemplary embodiment, removal of the lenticule also causes a flattening of the anterior surface of the cornea peripheral to the steepened central region, the flattened region correcting for myopia, as is shown in FIG. 13.

In this embodiment shown in FIG. 12, lenticule 601 has a meniscus shape, which corrects for myopia by flattening the anterior surface of the cornea when the lenticule is removed. In other embodiments clearly contemplated herein, however, the lenticule can be created with a shape that is configured to correct other refractive errors, such as hyperopia. For example, other lenticule shapes can be created that, when removed, remove more corneal tissue in the peripheral region of the pupil, causing an increase the curvature of the anterior surface of the cornea and correcting for hyperopia. The methods herein include any suitable lenticule shape, as long as it still causes an increase in curvature in a central region of the anterior surface of the cornea to provide near vision as described herein.

Extension 608 (shown in dashed lines) illustrates an imaginary extension surface of peripheral region 603 extending across central region 607. Extension 608 can be drawn for purposes of measuring central thickness 609 of central region 607. In this embodiment central thickness 609 is about 50 microns or less, and is measured as the greatest linear distance from extension 608 to posterior lenticule incision 603 in central region 607. Similar extension surfaces can be drawn regardless of the shape of peripheral region 603. For example, extension 608 could be a flat surface if peripheral region 603 is flat. In this embodiment central region 607 has an outer diameter 610 between 1 mm and 4 mm. In some embodiments lenticule 601 has an outermost diameter between 1 mm and 8 mm.

The exemplary method also includes removing the lenticule from the stroma, which causes an increase in the curvature of a central portion of the anterior surface of the cornea for near vision, wherein the increase in curvature of the central portion of the anterior surface of the cornea has a central elevation change. FIG. 13 illustrates cornea 600 after lenticule 601 has been removed through incision opening 605. Removal of lenticule 601 causes flattening of the cornea in peripheral region 612 to correct for myopia (due to the shape of the lenticule), but the central bump 607 created in the posterior lenticule incision 603 causes a region of increased relative curvature 611 in the anterior surface of the cornea, which provides near vision and corrects for presbyopia. Central elevation change 613 in the central region due to central bump region 607 is also illustrated, which as is described in more detail above. The posterior lenticule incision is illustrated in the cornea to illustrate the location of the incision after lenticule 601 has been removed.

In other embodiments an emmetrope can be treated by creating a lenticule that is equally thick across its width (optionally with a taper at the periphery), with the lenticule including a central bump as described herein.

As is described in more detail above, the methods of lenticule extraction that correct for presbyopia also take into consideration, and plan for, epithelial remodeling. The entire disclosure above related to taking epithelial remodeling therefore applies to the methods of lenticule extraction herein. For example, in this embodiment, central thickness 609 is about 50 microns or less measured from extension 608 and is 3 to 7 times the central elevation change 613. All of the other factors for procedure planning that are described above, are, however, applicable to central region 607.

In the embodiment in FIGS. 11-13 central region 607 is shown and described as being created in the posterior lenticule incision 603. In any of the methods herein, however, central bump region 607 can alternatively be created in a central region of the anterior lenticule incision 602. In these methods the thickness of the central bump region is measured from an imaginary extension of the anterior lenticule incision. In any of the methods herein, alternatively still, both the anterior lenticule incision and the posterior lenticule incision can have a central bump region thereon, with the part-bumps on each of the anterior lenticule incision and the posterior lenticule incision together being considered the central bump region. In any of these methods, the central bump region causes an increase in curvature in a central region of the anterior surface of the cornea to correct for near vision.

What is claimed is:

1. A method of correcting vision for presbyopia, comprising:
    remodeling the stroma with a laser to create an intracorneal shape, wherein the intracorneal shape includes a central region with a thickness that is about 50 microns or less measured from an extension of a shape of a peripheral region of the corneal shape,
    wherein remodeling a portion of the stroma increases a curvature of a central portion of the anterior surface of the cornea with a central elevation change for near vision while allowing distance vision in a region peripheral to the central portion;
    wherein the corneal shape compensates for epithelial remodeling of the epithelial layer of the cornea in response to remodeling the stroma, and wherein the central region with a thickness that is about 50 microns or less measured from an extension of a shape of the peripheral region of the corneal ablation shape is 3 to 7 times the central elevation change.

2. The method of claim 1 wherein the remodeling step is performed without ablating the stroma.

3. The method of claim 1 wherein the remodeling step creates a corneal lenticule, and the intracorneal shape is defined by a posterior lenticule incision.

4. A method of correcting vision for presbyopia, comprising:
    creating a lenticule in a stroma, wherein creating the lenticule includes creating an anterior lenticule incision and a posterior lenticule incision with a femtosecond laser, wherein one of the posterior lenticule incision and the anterior lenticule incision has a central region and a peripheral region, the central region having increased curvature relative to the peripheral region, and a central thickness that is about 50 microns or less measured from an extension of the peripheral region, the central region having an outer diameter between 1 mm and 4 mm; and
    removing the lenticule from the stroma, wherein removing the lenticule increases the curvature of a central portion of the anterior surface of the cornea with a central elevation change for near vision; wherein one of the posterior lenticule incision and anterior lenticule incision compensates for epithelial remodeling of the epithelial layer of the cornea in response to cutting and removing the lenticule in the stroma, and wherein the central thickness that is about 50 microns or less measured from an extension of the peripheral region is 3 to 7 times the central elevation change.

5. The method of claim 4 wherein creating the anterior lenticule incision comprises creating the anterior lenticule incision between 5 microns and 250 microns deep in the stroma.

6. The method of claim 4 wherein removing the lenticule comprises creating a corneal flap.

7. The method of claim 4 wherein the method of correcting vision does not include creating a corneal flap.

8. A method of correcting vision for presbyopia, comprising:
    creating a lenticule in a stroma, wherein creating the lenticule includes creating an anterior lenticule incision and a posterior lenticule incision with a femtosecond laser, wherein the posterior lenticule incision has a posterior peripheral region and a posterior central region, and the anterior lenticule incision has an anterior central region and an anterior peripheral region, the anterior and posterior central regions having increased curvature relative to the anterior and posterior peripheral regions, the anterior and posterior central regions having a combined thickness that is about 50 microns or less measured from extension of the peripheral regions, the anterior and posterior central regions having an outer diameter between 1 mm and 4 mm; and
    removing the lenticule from the stroma, wherein removing the lenticule increases the curvature of a central portion of the anterior surface of the cornea with a central elevation change for near vision; wherein the posterior lenticule incision and the anterior lenticule incision compensate for epithelial remodeling of the epithelial layer of the cornea in response to cutting and removing the lenticule in the stroma, and wherein the combined central thickness that is about 50 microns or less measured from extensions of the peripheral regions is 3 to 7 times the central elevation change.

* * * * *